US010395548B1

(12) United States Patent
Levis et al.

(10) Patent No.: US 10,395,548 B1
(45) Date of Patent: Aug. 27, 2019

(54) COMPUTER-BASED SYSTEM FOR RELATIONAL MODALITY ASSESSMENT WITH PROJECTIVE TESTING

(71) Applicants: Albert J. Levis, Manchester, VT (US); Maxwell E. Levis, Manchester, VT (US)

(72) Inventors: Albert J. Levis, Manchester, VT (US); Maxwell E. Levis, Manchester, VT (US)

( * ) Notice: Subject to any disclaimer, the term of this patent is extended or adjusted under 35 U.S.C. 154(b) by 100 days.

(21) Appl. No.: 15/396,283

(22) Filed: Dec. 30, 2016

Related U.S. Application Data

(60) Provisional application No. 62/273,998, filed on Dec. 31, 2015.

(51) Int. Cl.

| | |
|---|---|
| *G09B 7/06* | (2006.01) |
| *G09B 7/00* | (2006.01) |
| *G09B 7/10* | (2006.01) |
| *G09B 7/02* | (2006.01) |
| *G16H 10/20* | (2018.01) |

(52) U.S. Cl.
CPC ................ *G09B 7/00* (2013.01); *G09B 7/02* (2013.01); *G09B 7/10* (2013.01); *G16H 10/20* (2018.01)

(58) Field of Classification Search
CPC ........................................................ G09B 7/06
See application file for complete search history.

(56) References Cited

U.S. PATENT DOCUMENTS

| | | | |
|---|---|---|---|
| 5,702,253 | A | 12/1997 | Bryce et al. |
| 5,743,742 | A | 4/1998 | Morrel-Samuels |
| 5,980,447 | A | 11/1999 | Trudeau |
| 6,053,866 | A | 4/2000 | McLeod |
| 6,159,015 | A | 12/2000 | Buffington et al. |
| 6,338,628 | B1 | 1/2002 | Smith |
| 6,425,764 | B1 | 7/2002 | Lamson |
| 6,497,577 | B2 | 12/2002 | Kanter |

(Continued)

OTHER PUBLICATIONS

Levis, Albert J., "Conflict Analysis, The Formal Theory of Behavior", Normative Publications, Manchester Village, Vermont (1988).

(Continued)

*Primary Examiner* — James S. McClellan
(74) *Attorney, Agent, or Firm* — The Law Office of Patrick F. O'Reilly III, LLC

(57) ABSTRACT

A computer-based system for relational modality assessment with projective testing is disclosed herein. The system includes a computer operably associated with a local input device located proximate to the computer, a visual display device, and memory storing executable instructions. The computer is specially programmed to generate a relational inventory test comprising a plurality of questions pertaining to a plurality of diagnostic categories, and a projective sequence test comprising a plurality of artwork assignments and corresponding questionnaires pertaining to a plurality of role states. The computer is further specially programmed to generate a quantitative assessment from the testee's responses to the relational inventory test, and to generate a structured output report using the testee's artwork and responses to the questionnaires of the projective sequence test so that the testee is capable of self-diagnosing his or her psychological state.

20 Claims, 21 Drawing Sheets

(56) References Cited

U.S. PATENT DOCUMENTS

| | | | | |
|---|---|---|---|---|
| 6,722,885 | B2 | 4/2004 | Westh | |
| 6,767,213 | B2 | 7/2004 | Fleishman | |
| 7,033,181 | B1 | 4/2006 | Bennett et al. | |
| 8,147,251 | B1 * | 4/2012 | Anson | G16H 10/60 434/236 |
| 8,562,355 | B2 | 10/2013 | Snyder | |
| 2004/0148210 | A1 * | 7/2004 | Barrett | G06Q 30/0203 705/7.32 |
| 2005/0019734 | A1 | 1/2005 | Peled | |
| 2006/0160053 | A1 | 7/2006 | Swenson | |
| 2006/0281059 | A1 | 12/2006 | Trufant | |
| 2007/0048706 | A1 | 3/2007 | Tan | |
| 2008/0318563 | A1 * | 12/2008 | Ross | G06F 19/322 455/418 |
| 2010/0159427 | A1 | 6/2010 | Bachar | |
| 2010/0218118 | A1 | 8/2010 | Bronkema | |
| 2012/0150822 | A1 * | 6/2012 | Young | G06Q 90/00 707/690 |
| 2015/0379888 | A1 * | 12/2015 | Hill | G09B 7/06 434/236 |
| 2016/0078774 | A1 * | 3/2016 | Vardi | G09B 7/06 434/353 |

OTHER PUBLICATIONS

Levis, Albert J., "Conflict Analysis Training: A Program of Emotional Education", Normative Publications, Manchester Village, Vermont (1988).

* cited by examiner

3

1

Part 1: Dominant Cooperative Syndrome

| | | | | | | | |
|---|---|---|---|---|---|---|---|
| | **Leadership** | | | | | | |
| 1 | I demand that others cooperate with me. | 1 | 2 | 3 | 4 | 5 | 6 |
| 2 | If I think something is right, I'll do it, no matter what the rules are. | 1 | 2 | 3 | 4 | 5 | 6 |
| 3 | I maintain my image at any cost. | 1 | 2 | 3 | 4 | 5 | 6 |
| 4 | I have always been a leader and enjoy it. | 1 | 2 | 3 | 4 | 5 | 6 |
| 5 | I like to tell others what to do. | 1 | 2 | 3 | 4 | 5 | 6 |
| 6 | I am usually the peerson who initiated and who takes care of things in my relationships. | 1 | 2 | 3 | 4 | 5 | 6 |
| 7 | I make my needs known very clearly. | 1 | 2 | 3 | 4 | 5 | 6 |
| 8 | I feel other people would do a far better job under my supervision than on their own. | 1 | 2 | 3 | 4 | 5 | 6 |
| | **Competiveness and Dominance** | 1 | 2 | 3 | 4 | 5 | 6 |
| 9 | I get my way more than I give into others. | 1 | 2 | 3 | 4 | 5 | 6 |
| 10 | I am a dominant person. | 1 | 2 | 3 | 4 | 5 | 6 |
| 11 | I like to command power and authority over others. | 1 | 2 | 3 | 4 | 5 | 6 |
| 12 | I am very aware of how others dress, what they own and earn, where they live. | 1 | 2 | 3 | 4 | 5 | 6 |
| 13 | I have always been aware of who is ahead of me. | 1 | 2 | 3 | 4 | 5 | 6 |
| 14 | I have urges to do forbidden things. | 1 | 2 | 3 | 4 | 5 | 6 |
| 15 | I am boisterous and demonstrative. | 1 | 2 | 3 | 4 | 5 | 6 |
| 16 | I call attention to myself by speaking up a lot. | 1 | 2 | 3 | 4 | 5 | 6 |
| 17 | If I want to do something, I do it. | 1 | 2 | 3 | 4 | 5 | 6 |
| 18 | I have a comment all the time. | 1 | 2 | 3 | 4 | 5 | 6 |
| 19 | I'd like people to think I'm the greatest. | 1 | 2 | 3 | 4 | 5 | 6 |
| | **Personal Discomfort and Sensitivities** | 1 | 2 | 3 | 4 | 5 | 6 |
| 20 | My problem is one of guilt. | 1 | 2 | 3 | 4 | 5 | 6 |
| 21 | I tend to feel patronized when somebody gives me a compliment. | 1 | 2 | 3 | 4 | 5 | 6 |
| 22 | I do not let others take advantage of me. | 1 | 2 | 3 | 4 | 5 | 6 |

| CASE TITLE | PICTURE | WHO DO YOU INDENTIFY WITH? |
| --- | --- | --- |
| Case study#1 TRYING TO SURVIVE AS A DOG | 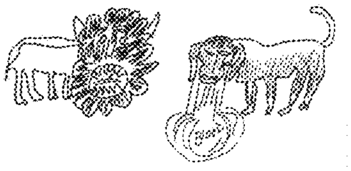 | "[I identify with] the dog – all he needs to do is to learn to live the life he has been given. He's never going to be a tiger! [This is] simply just a scenario between me and the strong people in my life." |
| Case #2 THE ELEPHANT AND THE BUTTERFLY | 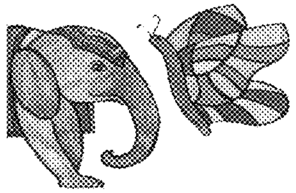 | "I can move like [the elephant] in terms of analyzing feelings and emotions and understanding how one needs to deal with responsibilities. You can't just keep on flying." |

FIG. 6

| | | | | | |
|---|---|---|---|---|---|
| Stress: Losing her loving grandmother. | Response: Mask is a bag over her head. | Anxiety: A list of traumas and negative feelings, followed by an empty heart. | Defense: Open mouth of a waif despises helpless, worthless bird with broken wing. | Reversal: Dreaming of teaching again. | Compromise: Sun and troll afraid of light, burning with flames over his head. |

| | DEFENSE | | REVERSAL | | COMPROMISE |
|---|---|---|---|---|---|
| Items | Animal Metaphor | Fairy Tale Metaphor | Animal Metaphor 2 | Dream Metaphor | Short Story Metaphor |
| Image | 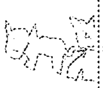 | 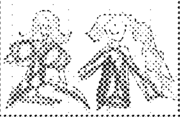 |  | 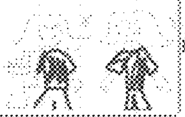 |  |
| | *The dog is adorable and friendly ...* | *Cinderella beautiful, sweet...* | *. bear, 40. female angry. Puppy, 8 male, timid, ...* | *used to be childhood friends. She was a liar and a theif* | *Kara,27,female fun, spontaneous, Marc,30,male. successful...* |
| Convers-ation | *dog 1 is saying... dog 2 is agreeing to...* | *Cinderella tells ... Rapunzel replies...* | *Bear - Stay away from my cubs.. Dog - But I am having fun ...* | *My memory of dreams are a bit choppy. This one recurring ...* | *Kara and Marc go on a vacation in Fiji... They come across an amazing yacht...* |
| Conflicts | *One dog is confident...* | *Rapunzel is jealous...Cinderella hates her family...* | *Bear is overly protective ...* | *I had fun hanging out ...She stole from me a few times...* | *They weren't quite sure if they loved each other ...* |
| Changes | *Dog 2 needs to speak up. Dog 1 needs to listen...* | *Cinderella needs to.... Rapunzel needs to...* | *Dog is fun loving...The bear only wants ...* | | *The bear needs to understand...The dog needs to...* |
| Identific-ation | *I have become more reserved...* | *Like Rapunzel, I need to find* | | | *Kara An ex-boyfriend* |
| Pertinenc e | *Dog 2 is me... Dog 1 are my friends...* | *I enjoyed watching Cinderella and Rapunzel....* | | *... my social life needs improvement....* | *Not having money makes me feel trapped...* |
| Personal Changes | *I should speak up more...* | *I should call out my brothers....* | *The bear needs to understand ...* | | *Get out of debt...stop with the self-pity.* |
| Pattern | *I tend to go with the flow ...* | *I would say debt has been an ...* | | *I don't sleep well and I tend to forget my dreams.* | *I am stuck on a treadmill... no adventu re.* |
| Respons-ibility | *I don't speak up for myself ...* | *Like Cinderella, I need to stand up for myself more ...* | | | *. I've gotten in trouble once or twice by...something mean.* |
| Willingnes s for Changes | *I will speak up for myself and be more...* | *I am willing to be more outspoken, honest with...* | | | *Not drink as much and think about what I say before I say it.* |

Letter To Your Self

| | |
|---|---|
| Transcript | **The testing experience feels like I am writing in a journal but using illustrations to really pull out the inner most thoughts that I have. I realize some of the turmoil I've been feeling and that I would like to have more direction and excitement in life.** |
| Relevance | **I plan on working on myself so that I am more confident, assertive and find ways to resolve conflicts with people in a diplomatic way without offending anyone.** |
| Changes | **Yes, I felt this was a very interesting survey and very unique in that I was instructed to make illustrations. It was interesting how the drawings were a reflection of how I feel sometimes.** |

Fig. 13

| | STRESS | | | RESPONSE | ANXIETY | |
|---|---|---|---|---|---|---|
| ITEMS | Childhood Conflict | Adolescent Conflict | ITEMS | Transparent Mask | Feelings Mask | What is in the Heart |
| Image |  |  | Image | 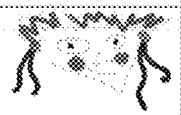 |  |  |
| What Happened | It was my mom yelling … | I broke curfew … | Emotions | Like Cinderella. I need to stand up for myself …. | worry, fatigue, scared, … | The heart is broken … |
| Feelings | I was scared of … | | Conflicts | not wanting to grow up… | feeling upset and anger… | the heart feels taken advantage… |
| Conflicts | She was angry with me for breaking … | | Resolution | to become more mature and responsible … | having the FBI track … | the heart wants to protect itself |
| Respons-ibility | …my fault for being a klutz | | | | | |
| Impact | when I would do something accidentally… | Imade me pretty angry at the time… | | | | |
| Suggested Changes | I apologize or pay … | | | | | |
| | Family Balloons | Recent Conflict | | Relationship Balloons | ITEMS | Mask Analysis |
| Image | 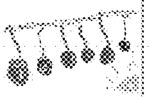 |  | | 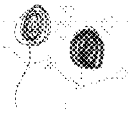 | Title | The Fake Mask covers up the Real Mask and its Heart |
| Members | | | | | Summary | The fake mask is the public … |
| Conversation | They are talking about… | I'm so angry and I am upset that… I have no control | | Balloon 1 - You look great… | Conclusions | The person hides their true feelings .. |
| Title | Balloons on a Picnic | | | My partner and I are on a midnight stroll… | Pertinence | I feel that I am the fake mask… |
| Conflicts | Brother balloon is teasing … | definitely affected me negatively…. | | Balloon 1 has a bit of a roaming … | Ideal Changes | I need to express myself more… |
| Changes | Both balloons should keep the criticism to themselves. | | | Balloon 2 could work on her confidence… | Realistic Changes | I may try to work out more, meditate more, from lawyers, the FBI, etc |

Fig. 14

Relational Modality Overall Scores

| Relational Modality | Overall Scores |
|---|---|
| Dominant Cooperative | **2.93** |
| Dominant Antagonistic | **2.89** |
| Submissive Cooperative | **3.89** |
| Submissive Antagonistic | **3.31** |
| Psychic Tension | **2.96** |

Fig. 15

Dominant Cooperative Scoring Profile

| Relational Modality | Weighted Average | Demanding (Stress) | Leadership (Response) | Competitive-ness (Anxiety) | Determina-tion (Defense) | Invulnerabi-lity (Reversal) | Outspoken-ness (Compromise) |
|---|---|---|---|---|---|---|---|
| Dominant Cooperative | 2.93 | 4 | 2.75 | 5.33 | 2.33 | 3 | 1.67 |

Fig. 16A

Dominant Antagonistic Scoring Profile

| Relational Modality | Weighted Average | Irreverence (Stress) | Territorialism (Response) | Explosiveness (Anxiety) | Self-Righteous-ness (Defense) | Insubordina-tion (Reversal) | Independence (Compromise) |
|---|---|---|---|---|---|---|---|
| Dominant Antagonistic | 2.89 | 2.17 | 3.71 | 2.5 | 2.45 | 3.71 | 4.33 |

Fig. 16B

*Submissive Cooperative Scoring Profile*

| Relational Modality | Weighted Average | Trustworthiness (Stress) | Selflessness (Response) | Flexibility (Anxiety) | Non-Confrontational (Defense) | Considerate-ness (Reversal) | Compliance (Compromise) |
|---|---|---|---|---|---|---|---|
| Submissive Cooperative | 3.89 | 3 | 4.25 | 4.67 | 4.32 | 2.83 | 2.5 |

Fig. 16C

*Submissive Antagonistic Scoring Profile*

| Relational Modality | Weighted Average | Disinterest-edness (Stress) | Hostility (Response) | Passivity (Anxiety) | Privacy (Defense) | Resignation (Reversal) | Self-Restraint (Compromise) |
|---|---|---|---|---|---|---|---|
| Submissive Antagonistic | 3.31 | 2.5 | 1.67 | 1.86 | 4.32 | 4.1 | 4.75 |

Fig. 16D

| Relational Modality | Weighted Average | Degree of Disability | Depression | Self-conscious Symptoms | Specific Conditions |
|---|---|---|---|---|---|
| Psychic Tension | 2.96 | 3.71 | 2.85 | 2.75 | 2.58 |

Fig. 16E

*Creativity Template*

<table>
<tr><th></th><th colspan="2">Emotions</th><th></th><th colspan="4">Behaviors</th></tr>
<tr><td rowspan="2">Stress</td><td>Childhood</td><td>Adolescent</td><td rowspan="2">Response</td><td rowspan="2">Balloon II</td><td colspan="3" rowspan="2">Mask I</td></tr>
<tr><td>Recent</td><td>Balloon</td></tr>
<tr><td>Anxiety</td><td>Mask II</td><td>Mask III</td><td>Defense</td><td>Animal Metaphor</td><td colspan="3">Fairy Tale</td></tr>
<tr><td>Reversal</td><td colspan="4">Animal Metaphor II</td><td>Dream</td><td>Compromise</td><td>Short Story</td></tr>
</table>

Fig. 17

*Insight Template*

| | Animal Metaphor | Fairy Tale Metaphor | Short Story |
|---|---|---|---|
| **Identification** | *I identify most with the tortoise. Like him, I prefer to remain alone and within my shell for the most part. Although many others will try to bring you out of that shell, that space where I can be alone and think to myself is what I prefer most.* | *I elaborate more with Shrek. Like him, I'm a loner who prefers solitude for the most part. And like Shrek, I have self-image issues, although in my case I am not a literal ogre so the world does not instantly write me off.* | *Jason, since I'm more cautious and generally not much of a risk taker* |
| **Pattern** | *There have been many times where I have felt compelled to go out with a group despite my best wishes so as to not let the group down. Recently, it was a friend's birthday and I went out with them despite having already wished them a happy birthday just so I could show support in person.* | *The other day I was asked to do some errands for a friend as a favor. At first I was resentful and only agreed to help out of a sense of guilt. However, by re framing my thoughts later on I was able to find some happiness in the act of helping a friend.* | *I chose to go out with my friend for Halloween despite my desire to stay inside recently. I went with my friend who wasn't comfortable going alone to a costume party. Although it made me uncomfortable and in the end I would have rather stayed home, I felt good after accompanying my friend for the night.* |
| **Pertinence** | *I identify and empathize with the tortoise. I also see how the rabbit is concerned for him and really just wants everyone to be a part of a harmonious group. In my life I often struggle with balancing my desire to be independent with the feelings of the collective group I'm involved with as a whole whether through school, work, or elsewhere.* | *I like the internal drama at the center of the tale. There is a woman who does not want to be a physical ogre, and an ogre who sees himself as such incarnate and has given up on the world. Through this tale, we are given a basic life lesson in that you are more alike your fellow human than you think. Sometimes I may see myself as an ogre but if you just go out and interact with others you'll find that most people just see you as a regular human too.* | *Like Jason, I often experience the conflict of wanting to remain in my comfort zone while at the same time not wanting to be selfish and inconsiderate of the group. Also like Jason, I'm often the one to concede. If it ends up being my decision vs. another's, I will usually give in and compromise if the other party is unwilling to.* |
| **Responsibility** | *I am willing to reach out to others more. And when they reach out to me, I have to do a better job of reciprocating their effort.* | *I tend to assume the worst in other people and think they assume the same about me. This general distrust has led me to be somewhat abrasive towards others and make them think I am just selfish when its really more that I just don't wish to put myself out there to the world.* | *I tend to put myself before others when it comes to social situations. Even though people may want or appreciate my company, I sometimes choose to deny them it out of selfishness.* |

Fig. 18

Growth: Suggested Changes Template

| | **Animal Metaphor** | **Fairy Tale** | **Short Story** |
|---|---|---|---|
| **Personal Change** | *There isn't much they can do besides accept each other for their respective natures.* | *By helping another, Shrek can learn the positives to bonding with others and hopefully confront his self-loathing. For Fiona, she must temper her brashness and learn to work with Shrek. By being more accommodating and less demanding of Shrek she can increase the level of trust between the two.* | *Like Jason in the story, I will continue to make personal sacrifices for my friends, even when it causes me anxiety or discomfort.* |
| **Willing-ness for Change** | *I am willing to reach out to others more. And when they reach out to me, I have to do a better job of reciprocating their effort.* | *I have to be more honest and open in my communication with others. If I can help I should, and if I can't I shouldn't just assume others are trying to use me for their own gain.* | *I am more willing to go out and socialize with good friends, even on nights where I might not be up to it or in a particularly social mood.* |

Fig. 19

Feedback Ratings

| Question | Rating (1-6) |
|---|---|
| The introductory essay was informative on the concept of the unconscious as a conflict resolving entity. | Agree |
| Which one of the following relational types do you identify with? A for Dorothy, dominant cooperative, B for the Lion, dominant antagonistic, C for the Scare Crow, submissive cooperative, and D for the Tin Man, submissive antagonistic? | Type D |
| The introductory essay provided clear information about the relational modality as wellness categories. | Agree |
| The introductory essay helped me understand the conflict resolution process as a sequence of six emotions: stress, response, anxiety, defense, reversal and compromise. | Neither Agree nor Disagree |
| The creativity component was therapeutic; the metaphors helped me to better understand myself and to also think of making changes. | Agree |
| The six-role template, combining images and text, integrates fragments of my life into a meaningful conflict resolution pattern. | Agree |
| It would be useful for me to have have a record of this program to remind me of my pattern of resolving conflicts and that changes I should make to improve relations and to decrease distress. | Agree |
| *The following items evaluate your experience with this program. Please answer the questions specifically in regard to the emotional education program and not the baseline measures.* ______ I felt this program was informative. | Agree |
| I felt this program clarified my sense of who I am. | Agree |
| After completing this program, I like myself better. | Neither Agree nor Disagree |
| I felt the program was respectful of who I am. | Agree |
| I felt this program helped me understand my personality. | Agree |
| I felt this program helped me gain understanding about my relational disposition. | Agree |
| The program was diagnostic. It helped me to identify my relational pattern. | Agree |
| Identifying my relational pattern helps me to better understand my self. | Agree |
| I was surprised by how much insight I gathered. | Disagree |
| This program was an emotional experience. | Agree |
| This program offered me new information about myself. | Neither Agree nor Disagree |
| This program helped me to identify changes to improve my relational pattern. | Agree |
| This program helped me identify how to better manage power. | Agree |
| I felt this program was not stigmatizing. | Agree |
| I think that this survey would be useful for high school students. | Agree |
| I think that this survey would be useful for clinical evaluations. | Agree |
| After taking this survey, I feel more motivated to make changes in my life. | Agree |
| The suggested value for taking this program should be: | $50 |
| I would like to repeat this program to see what changes I have made after: | 1 year |

Fig. 20

Summary of Letter To Your Self

| | |
|---|---|
| **Transcript** | *I feel that doing these exercises has led me to an emotional conclusion I already expected. I often reverted to similar themes and ideas in the prompts revolving around the conflict in myself between hiding and staying in my shell vs. making myself vulnerable and putting myself out there to the world. I know that it is a conflict that rests deep within me, but that the only to confront it is to take more chances and be a more active participant in my social relationships and the world around me.* |
| **Integration** | *I saw that there was a pattern to my way of thinking. For most of the tasks I kept thinking about what the emotions inside me were and why I kept going back to the inner conflict of man versus society. I could not detect the six-role dialectical process or relational modality while I was involved in the tasks, but I did sense that the tasks were making me think often about how much I shy from the world.* |
| **Relevance** | *My way of resolving conflict is to stop hiding from it. By shutting myself down so often emotionally I am only harming my ability to resolve conflict long-term. The only way to experience joy in life is to put yourself at risk of conflict, and by engaging others on a more emotional level I will better learn to communicate with and understand the people in my life.* |
| **Changes** | *It has helped me identify the link between my passiveness and current emotional conflicts in life. I now know that the only way for me to have more fulfilling relationships with others is to take off the mask I wear everyday and be more willing to show my true self to people.* |

Fig. 21

COMPUTER-BASED SYSTEM FOR RELATIONAL MODALITY ASSESSMENT WITH PROJECTIVE TESTING

CROSS-REFERENCE TO RELATED APPLICATIONS

This patent application claims priority to, and incorporates by reference in its entirety, U.S. Provisional Patent Application No. 62/273,998, entitled "Computer-Based System For Relational Modality Assessment With Projective Testing", filed on Dec. 31, 2015.

STATEMENT REGARDING FEDERALLY SPONSORED RESEARCH OR DEVELOPMENT

Not Applicable.

NAMES OF THE PARTIES TO A JOINT RESEARCH AGREEMENT

Not Applicable.

INCORPORATION BY REFERENCE OF MATERIAL SUBMITTED ON A COMPACT DISK

Not Applicable.

COPYRIGHT NOTICE

A portion of this disclosure contains material that is subject to copyright protection. The copyright owner has no objections to reproduction of the patent or disclosure documents, but otherwise reserves all copyrights, whatsoever.

BACKGROUND OF THE INVENTION

1. Field of the Invention

This invention generally relates to a computer-based system for relational modality assessment and projective testing, wherein the need for a professional psychologist or psychiatrist is reduced or eliminated.

2. Background and Description of Related Art

Personality assessments are delivered electronically and via the Internet for many purposes. They attempt to measure, assess, and interpret human behavior, feelings, and temperament. They can provide insight into an array of traits, including but not limited to personality traits, behavioral strengths and weaknesses, values, communication skills, and occupational interests. The output of these assessments can assist in improved personality self-awareness. They can also be used for the purpose of improving harmony and productivity related to small and large groups associated with families, businesses, schools, and government organizations.

There are many objective psychometric assessment tools administered via multiple choice-type questionnaires. Such tests have a restricted response format, such as allowing for true or false answers or rating using an ordinal scale. Examples of objective tests include the Keirsy Temerament Sorter, Myers-Briggs Type Indicator (MBTI), Minnesota Multiphasic Personality Inventory, Millon Clinical Multiaxial Inventory-III, Child Behavior Checklist, and the Beck Depression Inventory. For instance, The Keirsey Temperament Sorter attempts to reveal observable personality traits, such as habits of communication, patterns of action, and sets of trait attitudes, values, and talents. The Myers-Briggs Type Indicator (MBTI) assessment is a psychometric questionnaire designed to highlight psychological preferences that underlie a person's interests, needs, values, and motivation. The Minnesota Multiphasic Personality Inventory (MMPI) is used by trained professionals to assist in identifying personality structure and psychopathology. Analysis of the MMPI looks at relative elevation of factors compared to various clinical scales that include an established norm. Based on results, a personality or behavior profile is produced that can be compared to a profile that is considered normal for the purpose intended.

Still other psychological tests are projective, in that the content is analyzed for meaning rather than being based on presuppositions about meaning, as is the case with objective tests. Projective tests are used less often because they are more time consuming to administer. Some criticisms of projective tests include that they rely heavily on clinical judgment rather than norms and lack reliability and validity because they have no standardized criteria to which results may be compared. An example of a projective test is the Rorschach inkblot test in which a subject is shown a series of ten irregular but symmetrical inkblots, and asked to explain what they see. The subject's responses are then analyzed in various ways, noting not only what was said, but the time taken to respond, which aspect of the drawing was focused on, and how single responses compare to other responses for the same drawing. The Holtzman Inkblot is a variation of the Rorschach test. Its main differences lie in its scoring criteria as well as limiting subjects to one response per inkblot. Different variables such as reaction time are scored for an individual's response upon seeing an inkblot. Another projective test is the Thematic Apperception Test (TAT) in which an individual views ambiguous scenes of people. The subject is asked to describe various aspects of the scene, such as what led up to this scene, the emotions of the characters, and what might happen afterwards. The examiner then evaluates these descriptions, attempting to discover the conflicts, motivations and attitudes of the respondent. The above projective tests rely on feedback from a trained clinician. None of these projective tests are available online, and they all need the services of a psychologist observing the client. None of these projective tests are associated with a personality inventory, and they do not have a theoretical model understanding behavior as wellness relational modalities.

Scientists of psychology have evolved theoretical models over the ages in order to account for personality variations. Temperament theories have varied based on absolute and abstract formal parameters in order to explain personality differences. The earliest of distinctions were descriptive factors such as Galen's humors of the body and elements of nature such as earth, water, air, and temperature. Later factors were described as being more abstract like passivity and activity. None of the earliest models recognized the psyche as a complex multi-task entity having abstract measurable parameters.

Freud promoted personality variation using a variety of models. He evolved from identifying the unconscious as a repressed libidinal desire and aggression to identifying the unconscious as a three part structural entity: the id, ego, and super ego. His earliest theories led to the recognition of developmental phases of personality (oral, anal, phallic) while he later provided insights leading to observing relations, transference, and valuing the interpersonal field of personality manifestation. While Freud influenced the interpretation of traditional projective techniques, his theoretical models never led to an assessment procedure.

While Freud's work did not lead him to a personality typology, leading followers introduced such methodologies. Jung described extraversion versus introversion as two opposing forces, yet complementary. Homey developed theories for coping. She identified neurotic strategies used for reducing anxiety, which included "Moving toward", "Moving against", and "Moving away". Timothy Leary offered a map of interpersonal traits within a geometric circle that allows for comparison of different traits within the system. Theodore Millon developed personality diagnostic questionnaire tools. Eysneck identified biologically-based factors of neuroticism and psychoticism but confused formal distinctions with pathology, contaminating qualitative distinctions with quantitative parameters. The problem in these past formal typologies is they do not identify the several formal operations of the psyche as a systemic unit (formal relational mechanism) with adjustive functions that could lead to the psyche playing a role in personal conflict resolution.

The recognition of the formal relational mechanism can be traced to Aristotle, who constructed plots having several formal traits in Greek tragedies. The formal traits within the plots are not arbitrary but are viewed to have periodicity, patterns that repeat with relational systemic reasoning. His plays had a structure consisting of three parts, a beginning, middle, and end; the totality was characterized with 'continuity of action' and also having a moral function. The end of the play exhibited a relieving of emotions associated with the presence of an emissary of the gods, which the Romans called the Deus ex machine.

The 'Formal Theory' developed by Albert Levis rediscovered Aristotle's formal and moral holon as a periodic phenomenon with a scientific structure of energetic transformations, characterized by a conservation of energy and a directional ending coinciding with an increase in order. (Ref: Levis, Albert J. (1988) Conflict Analysis, The Formal Theory of Behavior. Manchester Village, Vt.: Normative Publications.) Levis identifies the process as a three-oscillation harmonic with a six-role sequence. The six-role sequence is the syntax of the emotions: stress is followed by response, anxiety by defense, and reversal by compromise. The emotions are interrelated energies that form the well-organized symbolic universe of the unconscious. The unconscious is recognized as an equilibrial homeostatic phenomenon maintaining the feelings of the person in normative balance. Its function compels the individual to make adjustments to what it perceives as deviations from the norm. Deviations from the norm are experienced as conflicts generating motivational forces pursuing restoration of the rest state. Therefore, the function of the unconscious is reducing psychic tension in the service of social adjustment. The Levis methodology teaches that deviations from the norm, which cause psychic tension, are measureable, qualifiable, and quantifiable, abiding by the laws of science and logic.

The six-role sequence is directed by three mandatory formal operations: passivity transforming to activity, antagonism to cooperation, and alienation to mutual respect. The sequence is predictable, starting with chaos and ending with order, defining a moral order that results in conflict resolution. Scientifically, resolutions are energetic transformations. The energy conserved in the Levis theory becomes enhanced and is more coherent. It is defined as the moral order and is experienced as an attitude change and an improved sense of meaning. The assessment's inventory allows to identify the personal formal relational path to conflict resolution.

The sequence of emotions experienced in the unconscious conflict resolution process is manifest as a syndrome of interrelated emotions and behaviors corresponding to the six role states. This sequence of six role states may be reduced to the formal variations of one key or self-recognizable activity that may unfold intra-psychically as thoughts or associations. Interpersonally, the thoughts or associations are seen as a system of reciprocal interactions. Syndromes then consist of the constellation of the six formally interrelated role states as emotions and behaviors bound together as a relational pattern beginning with a stressor and ending with a resolution. Syndromal sequences vary as conflict resolutions differ qualitatively along the three guiding formal operations: reciprocity, negation and correlation.

Accordingly, the formal operation of reciprocity determines two alternative responses: the dominant and submissive relating; the formal operation of negation qualifies each one of the two along the opposite directions of cooperation and antagonism. Thus we recognize four relational modalities, dominance and submissiveness also cooperative and antagonistic variations. These four entities represent four diagnostic categories, the personality types. The third formal operation, correlation, reflecting how the individual relates to the public, as alienated versus mutually respectful allows a quantitative measurement of the individual's psychic tension, reflecting the intensity of conflict experienced as maladjustment or neuroticism; this is the mental status scale, pertaining to the intensity of conflict or anxiety experienced. This variable is independent of the four relational modalities. While operations may be viewed as qualitative distinctions, they are also modified to reflect intensity of responses, as the quantitative determination of dominance, submission, cooperation, antagonism and psychic tension.

The four relational personality modalities are wellness distinctions, not stigmatizing psychiatric diagnoses. They are genetically determined qualifiers of wellness. Yet these wellness states account for psychopathology, illness. The formal structure of the syndromes establishes a cause effect interrelation of emotions and behaviors. This personality typology clarifies individual emotional perceptions and distortions, as well as choice of behavioral responses. Thus the diagnostic categories account for the etiological formulation of pathology. Dominance may lead to anxiety, defensiveness, while submissiveness may lead to depression and to hostility. The formal connection of emotions intensified by stressors explains pathogenesis. This interrelation accounts for psychopathology as the intensification or polarization of relations experienced intra-psychically and interpersonally.

Recognizing one's relational pattern explains the personal experiences, symptoms as well as emotions, as parts of a syndrome. One's sensitivities, actions, reactions, anxieties, defenses, reversals and resolutions or compromises are components of the syndrome. The relational diagnosis connects disparate personal and interpersonal experiences; it makes them meaningful by explaining their connection as emotions, defenses, reversals, and the underlying pattern of the six role states.

This structure of emotions entails the direction for making responsible changes in dealing with stressors, averting helplessness, while assuming corrective intervention in power-management. Awareness of one's relational diagnosis provides the direction of emotional behavioral changes in terms of what one can do to reduce anxiety as anticipations of role reversal, and of defensiveness leading to actual reversals.

Although there are many computerized personality inventory assessment instruments, there is a lack of projective tests through the online delivery mode. There is a need for a more reliable and consistent self-assessment test that will offer, not only relational distinctions, but also like the projective tests, reliable insights on the person's thinking for the purpose of understanding internal conflicts on an individual or group basis.

The problem with conventional computerized assessment tools is that they can be unreliable, producing varying results in consecutive retesting. The reason for the inconsistency is the dependency on content and methods that rely heavily on external symptoms rather than an interconnection of personal emotions that provide insights on the identified four relational modality patterns as the wellness relational diagnoses.

There is a need for a computer-based psychological assessment tool that increases self-awareness and reduces the perception of helplessness and passivity in dealing with one's emotions. The patient/client, who realizes the syndromal interconnection of emotions and behaviors, is more likely to assume responsibility for the experience and is more likely to seek deliberately to correct it. Along with this self-awareness and self-assumed responsibility comes a reduced need to depend on chemically based treatments or outside experts' services.

There is a need for a computer-based psychological assessment tool that does not solely rely on objective testing of traits and symptoms but includes one or more self-assessment projective tests combined with a relational inventory leading to syndromal self-analysis.

There is a need for an easily obtainable psychological assessment tool that is self-revealing where the testee does not require expensive professional oversight; where the testee creates his/her own art during the assessment via a computer graphics program that communicates directly with the assessment tool in real-time.

Finally, there is a need for a computer-based psychological assessment tool that produces an output report to the patient/client in the form of a comprehensive and personalized narrative that includes their own acknowledgment of personal stress, response to stress, symptoms of anxiety, defense mechanisms, reversals in positions of power, and redemption through completion of compromises. The report includes the self-generated art that provides insights into one's own patterns of conflict thus increasing the probability of assuming responsibility for making changes. This approach does not require professional assistance, is accomplished in one sitting, is cost effective, and expedites the process of psychotherapy and also of psychoeducation as a wellness emotional training.

BRIEF SUMMARY OF EMBODIMENTS OF THE INVENTION

Accordingly, the present invention is directed to a computer-based system for relational modality assessment with projective testing that substantially obviates one or more problems resulting from the limitations and deficiencies of the related art.

In accordance with one or more embodiments of the present invention, there is provided a computer-based system for relational modality assessment with projective testing. The system includes a computer system comprising a computer operably associated with a local input device located proximate to the computer, a visual display device, and memory storing executable instructions. The computer is specially programmed to perform the operations of: (i) generating a relational inventory test comprising a plurality of questions pertaining to a plurality of diagnostic categories, and displaying the plurality of questions of the relational inventory test on the visual display device so that the plurality of questions are viewable by a system user; (ii) receiving, at the local input device, answers to the plurality of questions of the relational inventory test from the system user; (iii) generating a quantitative assessment of one or more of the plurality of diagnostic categories based upon the answers of the system user to the plurality of questions of the relational inventory test; (iv) outputting the quantitative assessment of the one or more of the plurality of diagnostic categories for the system user on the visual display device; (v) generating a projective sequence test comprising a plurality of artwork assignments and corresponding questionnaires pertaining to a plurality of role states, and displaying the artwork assignments and the corresponding questionnaires of the projective sequence test on the visual display device so that the artwork assignments and the corresponding questionnaires are viewable by a system user; (vi) receiving, at the local input device, a plurality of drawings elicited by the artwork assignments and a plurality of responses to the corresponding questionnaires from the system user; (vii) generating a structured output report pertaining to one or more of the plurality of role states based upon the plurality of drawings and the plurality of responses of the system user to the plurality of artwork assignments and the corresponding questionnaires of the projective sequence test; and (viii) outputting the structured output report pertaining to the plurality of role states for the system user on the visual display device. Based upon the quantitative assessment generated from the results of the relational inventory test and the structured output report generated from the results of the projective sequence test, the system user is capable of self-diagnosing his or her psychological state.

In a further embodiment of the present invention, the plurality of questions of the relational inventory test includes subsets of questions directed to particular relational characteristics, wherein the answers to the plurality of questions of the relational inventory test comprise numerical level of agreement values, and wherein, prior to the operation of generating the quantitative assessment of the one or more of the plurality of diagnostic categories, the computer is further specially programmed to perform the operation of: (ix) computing one or more numerical averages of the numerical level of agreement values corresponding to respective one or more particular relational characteristics.

In yet a further embodiment, after the operation of computing one or more numerical averages of the numerical level of agreement values corresponding to the respective one or more particular relational characteristics, the computer is further specially programmed to perform the operation of: (x) computing one or more additional numerical averages for one or more of the plurality of diagnostic categories using the one or more numerical averages computed for the one or more particular relational characteristics.

In still a further embodiment, the quantitative assessment of the one or more of the plurality of diagnostic categories is based upon the one or more additional numerical averages computed for the one or more of the plurality of diagnostic categories, and wherein the operation of generating the quantitative assessment of the one or more of the plurality of diagnostic categories comprises generating a graphical results summary of the relational inventory test that describes characteristics of the psychological state of the system user.

In yet a further embodiment, after the operation of generating the graphical results summary of the relational inventory test, the computer is further specially programmed to perform the operation of: (xi) generating, based upon the one or more computed additional numerical averages for the one or more of the plurality of diagnostic categories, one or more diagnostic narratives corresponding to respective ones of the one or more computed additional numerical averages; and (xii) outputting the one or more diagnostic narratives on the visual display device so that the one or more diagnostic narratives are viewable by the system user.

In still a further embodiment, the plurality of diagnostic categories of the plurality of questions of the relational inventory test comprise a plurality of categories corresponding to respective relational modalities and a category pertaining to psychic tension and/or wellness.

In yet a further embodiment, the plurality of role states of the projective sequence test comprises information on all six role states: (i) stress, (ii) response, (iii) anxiety, (iv) defense, (v) reversal, and (vi) compromise.

In still a further embodiment, the projective sequence test comprises a plurality of individual projective subtests, each of the plurality of individual projective subtests pertaining to one of the plurality of role states.

In yet a further embodiment, the plurality of individual projective subtests comprises at least one of: (i) a subtest pertaining to a childhood conflict, (ii) a subtest pertaining to an adolescent conflict, (iii) a subtest pertaining to a transparent mask of testee, (iv) a subtest pertaining to a feelings mask of the testee, (v) a subtest pertaining to what is in the heart of the testee, (vi) a subtest pertaining to a first type of animal metaphor, (vii) a subtest pertaining to a second type of animal metaphor, (viii) a subtest pertaining to a fairy tale metaphor, (ix) a subtest pertaining to a dream metaphor, and (x) a subtest pertaining to a short story metaphor; and each of the plurality of artwork assignments and the corresponding questionnaires pertain to a respective one of the individual projective subtests.

In still a further embodiment, after the operation of receiving the plurality of drawings elicited by the artwork assignments and the plurality of responses to the corresponding questionnaires from the system user, the computer is further specially programmed to perform the operation of: (ix) generating, based upon the plurality of responses to the corresponding questionnaires, one or more projective narratives that at least partially describe the psychological state of the system user; and (x) outputting the one or more projective narratives on the visual display device so that the one or more projective narratives are viewable by the system user.

In yet a further embodiment, the local input device comprises at least one of: (i) a mouse, (ii) a keyboard, and (iii) a digital pen or stylus.

In still a further embodiment, the operation of receiving the plurality of drawings elicited by the artwork assignments comprises receiving the plurality of drawings generated by the mouse.

In yet a further embodiment, the operation of receiving the plurality of drawings elicited by the artwork assignments comprises receiving the plurality of drawings generated by the digital pen or stylus.

In still a further embodiment, the local input device comprises a scanner device, and wherein the operation of receiving the plurality of drawings elicited by the artwork assignments comprises receiving the plurality of drawings uploaded using the scanner device.

In accordance with one or more other embodiments of the present invention, there is provided a computer-based system for relational modality assessment with projective testing. The system including a computer system comprising a computer operably associated with a local input device located proximate to the computer, a visual display device, and memory storing executable instructions. The computer being specially programmed to perform the operations of: (i) generating a relational inventory test comprising a plurality of questions pertaining to a plurality of diagnostic categories, the plurality of diagnostic categories of the plurality of questions including a plurality of categories corresponding to respective relational modalities and a category pertaining to psychic tension and/or wellness, and displaying the plurality of questions of the relational inventory test on the visual display device so that the plurality of questions are viewable by a system user; (ii) receiving, at the local input device, answers to the plurality of questions of the relational inventory test from the system user; (iii) generating a quantitative assessment of one or more of the plurality of diagnostic categories based upon the answers of the system user to the plurality of questions of the relational inventory test; (iv) outputting the quantitative assessment of the one or more of the plurality of diagnostic categories for the system user on the visual display device; (v) generating a projective sequence test comprising a plurality of artwork assignments and corresponding questionnaires pertaining to a plurality of role states, the plurality of role states including at least one of: (a) stress, (b) response, (c) anxiety, (d) defense, (e) reversal, and (f) compromise, and displaying the artwork assignments and the corresponding questionnaires of the projective sequence test on the visual display device so that the artwork assignments and the corresponding questionnaires are viewable by a system user; (vi) receiving, at the local input device, a plurality of drawings elicited by the artwork assignments and a plurality of responses to the corresponding questionnaires from the system user; (vii) generating a structured output report pertaining to one or more of the plurality of role states based upon the plurality of drawings and the plurality of responses of the system user to the plurality of artwork assignments and the corresponding questionnaires of the projective sequence test; and (viii) outputting the structured output report pertaining to the plurality of role states for the system user on the visual display device. Based upon the quantitative assessment generated from the results of the relational inventory test and the structured output report generated from the results of the projective sequence test, the system user is capable of self-diagnosing his or her psychological state.

In a further embodiment of the present invention, the plurality of questions of the relational inventory test includes subsets of questions directed to particular relational characteristics, wherein the answers to the plurality of questions of the relational inventory test comprise numerical level of agreement values, and wherein, prior to the operation of generating the quantitative assessment of the one or more of the plurality of diagnostic categories, the computer is further specially programmed to perform the operation of: (ix) computing one or more numerical averages of the numerical level of agreement values corresponding to respective one or more particular relational characteristics.

In yet a further embodiment, after the operation of computing one or more numerical averages of the numerical level of agreement values corresponding to the respective one or more particular relational characteristics, the computer is further specially programmed to perform the operation of: (x) computing one or more additional numerical averages for one or more of the plurality of diagnostic categories using the one or more numerical averages computed for the one or more particular relational characteristics.

In still a further embodiment, the quantitative assessment of the one or more of the plurality of diagnostic categories is based upon the one or more additional numerical averages computed for the one or more of the plurality of diagnostic categories, and wherein the operation of generating the quantitative assessment of the one or more of the plurality of diagnostic categories comprises generating a graphical results summary of the relational inventory test that describes characteristics of the psychological state of the system user.

In yet a further embodiment, after the operation of generating the graphical results summary of the relational inventory test, the computer is further specially programmed to perform the operation of: (xi) generating, based upon the one or more computed additional numerical averages for the one or more of the plurality of diagnostic categories, one or more diagnostic narratives corresponding to respective ones of the one or more computed additional numerical averages; and (xii) outputting the one or more diagnostic narratives on the visual display device so that the one or more diagnostic narratives are viewable by the system user.

In still a further embodiment, the projective sequence test comprises a plurality of individual projective subtests, each of the plurality of individual projective subtests pertaining to one of the plurality of role states.

In yet a further embodiment, the plurality of individual projective subtests comprises at least one of: (i) a subtest pertaining to a childhood conflict, (ii) a subtest pertaining to an adolescent conflict, (iii) a subtest pertaining to a transparent mask of testee, (iv) a subtest pertaining to a feelings mask of the testee, (v) a subtest pertaining to what is in the heart of the testee, (vi) a subtest pertaining to a first type of animal metaphor, (vii) a subtest pertaining to a second type of animal metaphor, (viii) a subtest pertaining to a fairy tale metaphor, (ix) a subtest pertaining to a dream metaphor, and (x) a subtest pertaining to a short story metaphor; and each of the plurality of artwork assignments and the corresponding questionnaires pertain to a respective one of the individual projective subtests.

In still a further embodiment, after the operation of receiving the plurality of drawings elicited by the artwork assignments and the plurality of responses to the corresponding questionnaires from the system user, the computer is further specially programmed to perform the operation of: (ix) generating, based upon the plurality of responses to the corresponding questionnaires, one or more projective narratives that at least partially describe the psychological state of the system user; and (x) outputting the one or more projective narratives on the visual display device so that the one or more projective narratives are viewable by the system user.

In yet a further embodiment, the local input device comprises at least one of: (i) a mouse, (ii) a keyboard, and (iii) a digital pen or stylus.

In still a further embodiment, the operation of receiving the plurality of drawings elicited by the artwork assignments comprises receiving the plurality of drawings generated by the mouse.

In yet a further embodiment, the operation of receiving the plurality of drawings elicited by the artwork assignments comprises receiving the plurality of drawings generated by the digital pen or stylus.

In still a further embodiment, the local input device comprises a scanner device, and wherein the operation of receiving the plurality of drawings elicited by the artwork assignments comprises receiving the plurality of drawings uploaded using the scanner device.

It is to be understood that the foregoing general description and the following detailed description of the present invention are merely exemplary and explanatory in nature. As such, the foregoing general description and the following detailed description of the invention should not be construed to limit the scope of the appended claims in any sense.

BRIEF DESCRIPTION OF THE SEVERAL VIEWS OF THE DRAWINGS

The invention will now be described, by way of example, with reference to the accompanying drawings, in which:

FIG. 1 illustrates exemplary questions from the relational inventory (RI) test that are categorically arranged in accordance with their communicative and relational characteristics, according to an embodiment of the invention;

FIG. 6 illustrates exemplary responses of a testee to one of the artwork assignments of the projective sequence test, where the testee is instructed to draw two (2) animals side-by-side as part of an animal metaphor subtest, according to an embodiment of the invention;

FIG. 13 illustrates a first portion of an exemplary output report generated from the artwork and responses of the testee to the projective sequence test, according to an embodiment of the invention;

FIG. 14 illustrates a second portion of the exemplary output report generated from the artwork and responses of the testee to the projective sequence test, according to an embodiment of the invention;

FIG. 15 illustrates an exemplary tabular summary of the overall scores for each relational modality generated from the answers to the questions of the relational inventory test, according to an embodiment of the invention;

FIG. 16A illustrates an exemplary tabular summary of the scores for the dominant cooperative relational modality generated from the answers to the questions of the relational inventory test, according to an embodiment of the invention;

FIG. 16B illustrates an exemplary tabular summary of the scores for the dominant antagonistic relational modality generated from the answers to the questions of the relational inventory test, according to an embodiment of the invention;

FIG. 16C illustrates an exemplary tabular summary of the scores for the submissive cooperative relational modality generated from the answers to the questions of the relational inventory test, according to an embodiment of the invention;

FIG. 16D illustrates an exemplary tabular summary of the scores for the submissive antagonistic relational modality generated from the answers to the questions of the relational inventory test, according to an embodiment of the invention;

FIG. 16E illustrates an exemplary tabular summary of the scores for the psychic tension relational modality generated from the answers to the questions of the relational inventory test, according to an embodiment of the invention;

FIG. 17 illustrates an exemplary tabular summary of the artwork assignments of the projective test organized in accordance with the six interrelated emotions, according to an embodiment of the invention;

FIG. 18 illustrates an exemplary tabular summary of insightful information generated from the answers to several questionnaires of the projective test, according to an embodiment of the invention;

FIG. 19 illustrates an exemplary tabular summary of suggested changes generated from the answers to several questionnaires of the projective test, according to an embodiment of the invention;

FIG. 20 illustrates an exemplary query report eliciting the testee's feedback regarding the computer-based assessment tool, according to an embodiment of the invention; and FIG. 21 illustrates an exemplary tabular summary of the testee's self-evaluation of the assessment's insight evoking experience, according to an embodiment of the invention.

Throughout the figures, the same elements are always denoted using the same reference characters so that, as a general rule, they will only be described once.

DETAILED DESCRIPTION OF EMBODIMENTS OF THE INVENTION

In accordance with an illustrative embodiment, the computer-based system generates both a personality inventory and one or more projective tests. The personality inventory results in a computer-generated narrative describing a prevalent relational modality, or mixture of modalities. The projective tests, combined with the personality inventory, are self-interpreted by the use of strategic questions about the art generated by the testee. Self-drawn art and answers to the questions are stored by the computer and compared to the personality inventory. As the testee reads the narrative as a result of completing both the personality inventory and the projective tests, the testee concludes on one's pattern of relating and how to seek to make changes in one's attitude. The sequence of events for the illustrative embodiment of the invention is depicted in FIG. 11.

Figure 11:
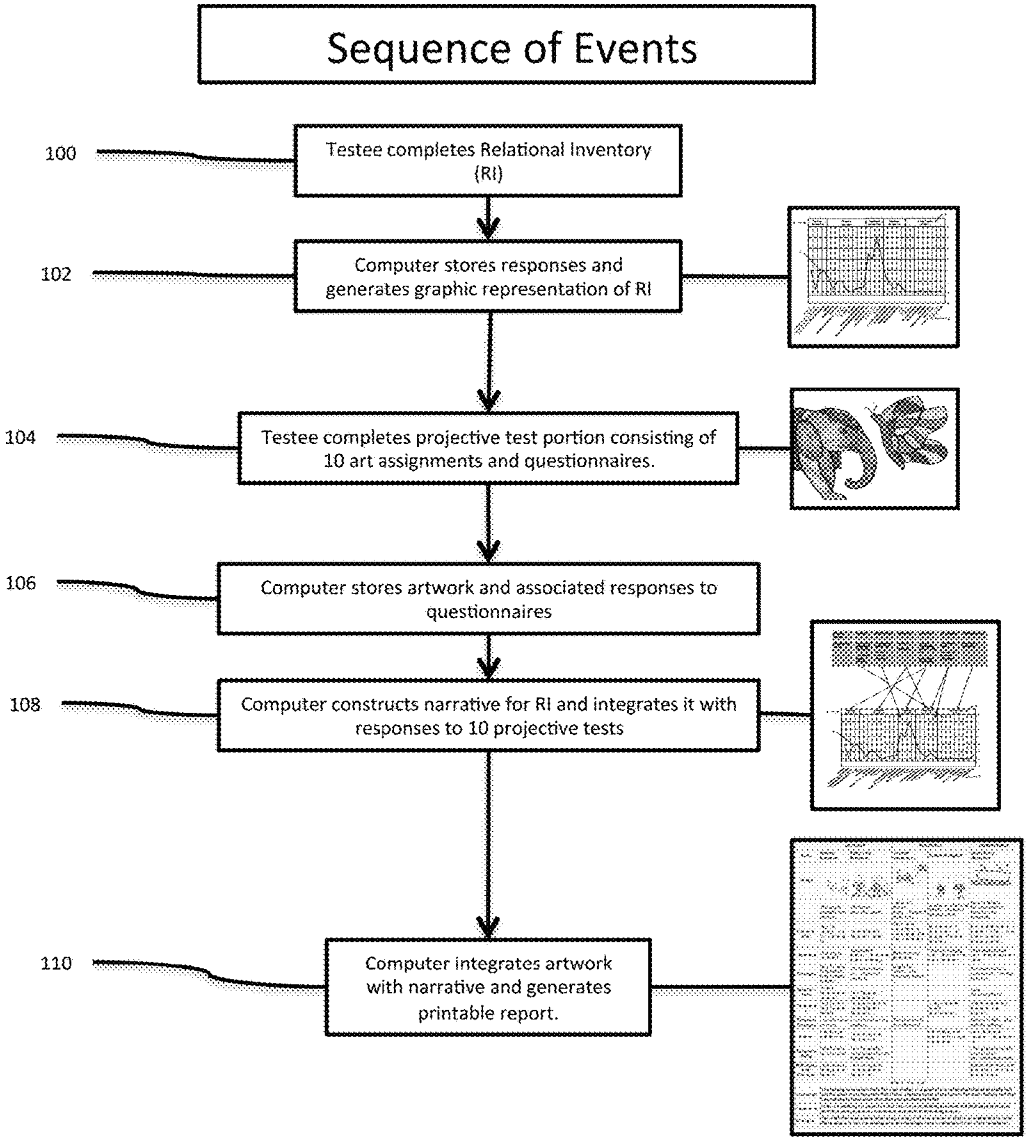
FIG. 11 is a flowchart illustrating the overall sequence of events carried out in conjunction with the computer-based testing system described herein, according to an embodiment of the invention.

Referring to FIG. 11, it can be seen that, in step 100 of the illustrative embodiment, the testee initially completes the relational inventory (RI) test. Then, in step 102, the computer stores the responses and generates a graphical representation of the relational inventory (RI) test. After which, in step 104, the testee completes the projective test portion that includes ten (10) artwork assignments and questionnaires pertaining to the artwork assignments. In step 106, after the testee has completed the projective test portion, the computer stores the artwork and associated responses to the questionnaires. Then, in step 108, the computer constructs a narrative for the relational inventory (RI) test, and integrates it with the responses to the ten (10) projective tests. Finally, in step 110, the computer integrates the artwork with the narrative and generates a printable report.

1. The Relational Inventory (RI) Test

Figure 2:
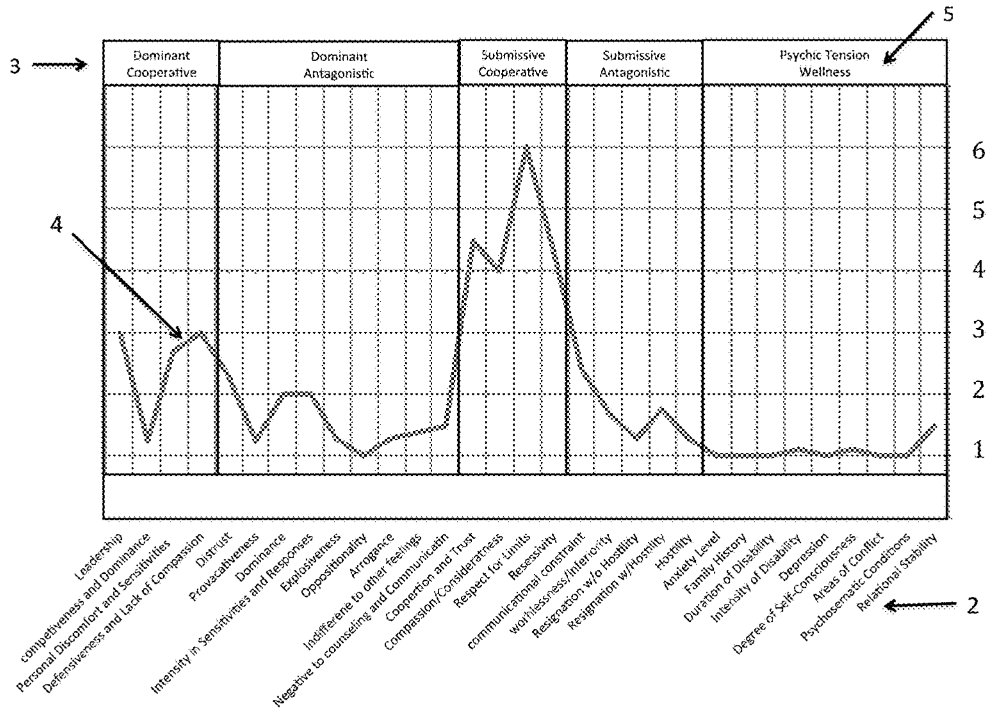
FIG. 2 illustrates exemplary graphical results generated from the answers to the questions of the relational inventory test, according to an embodiment of the invention.

In accordance with the illustrative embodiment, the relational inventory (RI) test comprises about 200 questions 1 where each is pre-assigned to a communicational and relational trait 2 as shown in FIG. 1. Specific personality traits are grouped as communicative and relational characteristics 2, and are pre-assigned to one of four relational modalities and the psychic tension wellness diagnostic categories 3, as shown in FIG. 2. The testee answers questions 1 by clicking on a number representing a level of agreement or disagreement along a scale 1-6 (e.g., by using the mouse of the computer). The computer then stores the responses.

There are four diagnostic categories, the relational modalities corresponding to the two dichotomies: dominance versus submissive, and cooperation versus antagonism. The fifth scale identifies the mental status corresponding to the intensity of unresolved conflicts measured as the psychic tension. The numbers of the relational profile reveal to the testee, at a glance, the relational modality and the psychic tension currently experienced.

The result may be displayed graphically as shown in FIG. 2, reflecting the individual's deviations by a line 4. The end segment 5 of the relational scale (RS) reflects the person's psychic tension state or degree of anxiety resulting in a diagnosis of wellness versus illness.

Figure 3:
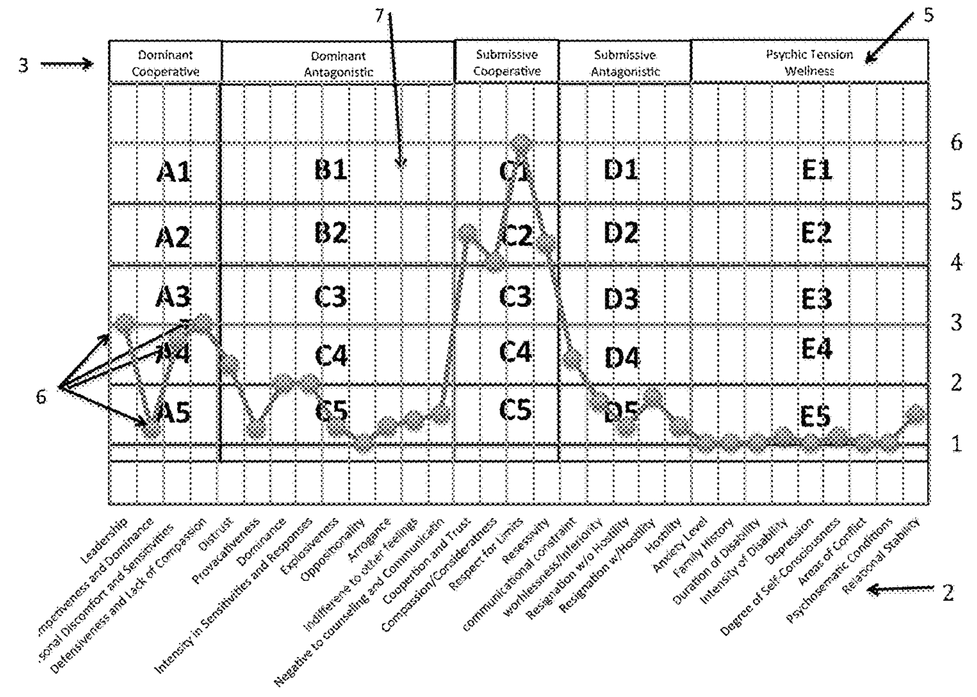
FIG. 3 illustrates the exemplary graphical results of FIG. 2, wherein each of the diagnostic and psychic tension wellness categories are divided into sections so that the section of each category, which is representative of the testee's responses, may be determined.

Based on the graphical nature of the result, the computer is able to construct a narrative summarizing the identified relational diagnosis of the testee while also reporting on the numerical values of the related relational traits. The relational modality of the testee is represented by a line 4, which is constructed by taking an average of relational items 1, within categories of the communicational and relational characteristics 2, and further combined into five diagnostic categories consisting of (a) dominant-cooperative, (b) dominant-antagonistic, (c) submissive-cooperative, (d) submissive-antagonistic, and (e) psychic tension-wellness as shown in FIG. 3. The benefit of a graphic output is experienced when a testee has previously taken the test, pursued a self-imposed plan of improvement, and decides to take the test again, at a much later date. Overlaying the results of the relational inventory (RI) in graphical form provides immediate feedback on degree of improvement.

Figure 4:
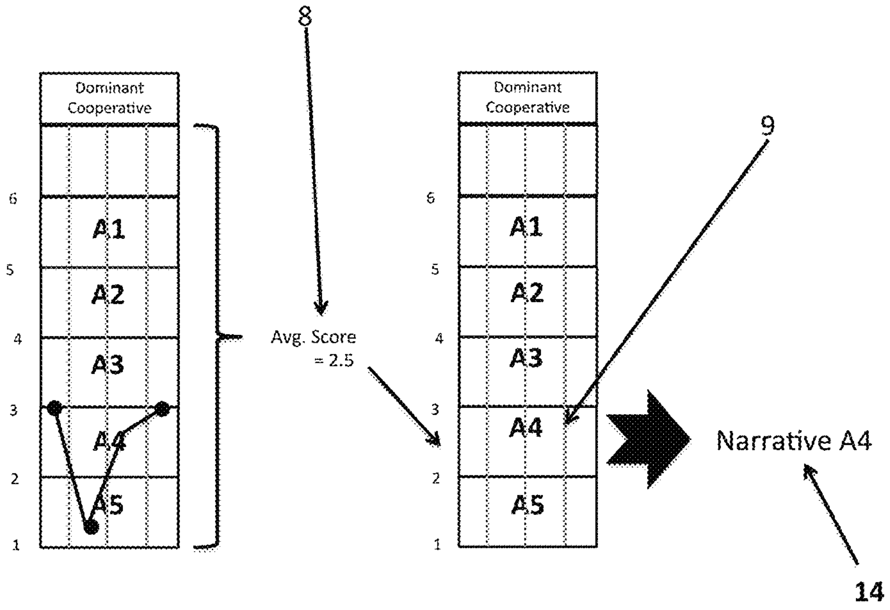
FIG. 4 illustrates the exemplary manner in which the arithmetic average for the four characteristics that make up the Dominant-Cooperative category is calculated, and the manner in which the section of this category, which is representative of the testee's responses, is determined, according to an embodiment of the invention.

Each diagnostic category 3 has six levels of differentiation ranging from 1-6, (y-axis) resulting in sections 7 labeled A1 thru E5 (see FIG. 3). The computer calculates an average score, based on testee responses, for each communicational and relational characteristic 2. Each average score is shown as a dot 6 as shown in FIG. 3. In order to determine which section 7 is representative of the testee's responses for any given diagnostic category 3, the computer calculates a second arithmetic average by adding the scores previously calculated for each relational characteristic within each diagnostic category 3, then dividing by the number of results previously stored by the computer for that diagnostic category 3. For instance, the arithmetic average for the four characteristics that make up the Dominant-Cooperative category in FIG. 4 is 2.5, denoted by reference numeral 8. The value of 2.5 corresponds to section A4 represented by reference numeral 9 in FIG. 3. Section A4, in turn, represents a preprogramed diagnostic written response 14, corresponding to the relational items (see FIG. 4).

Figure 5:
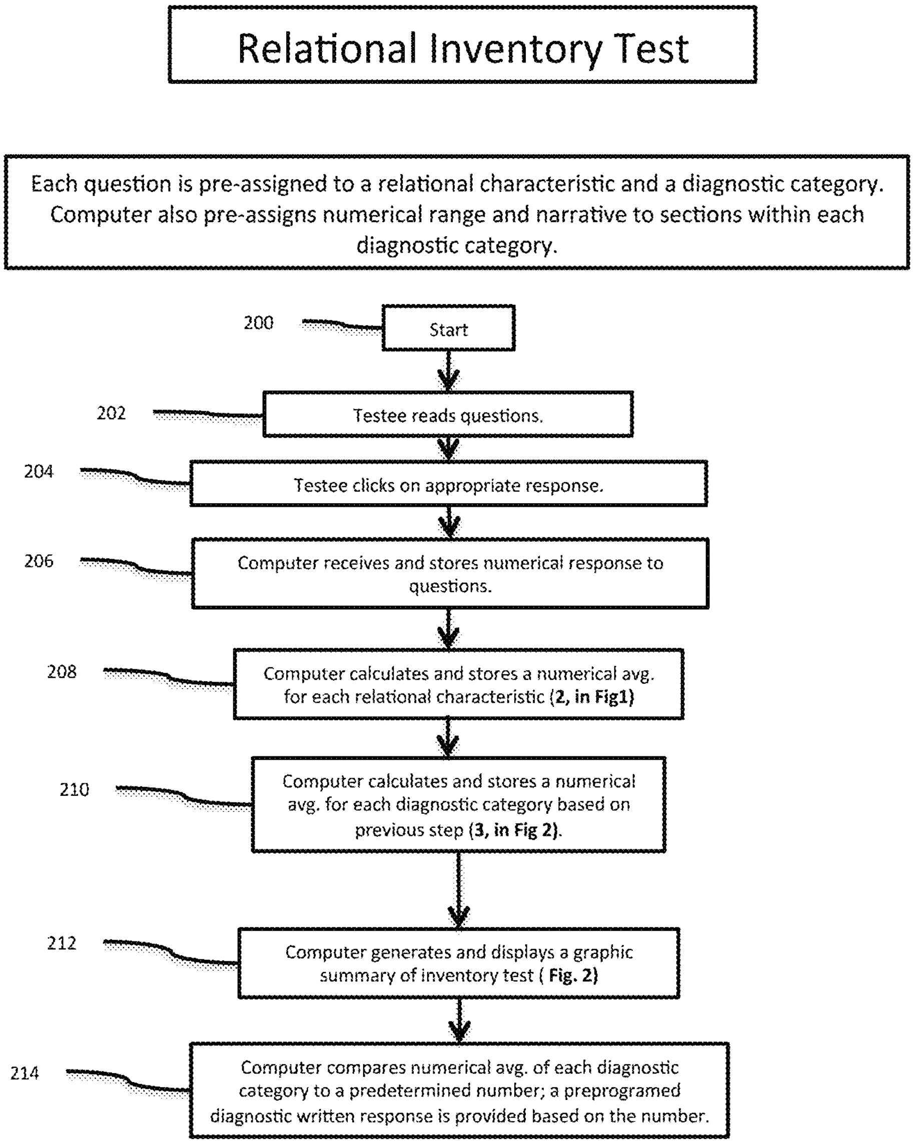
FIG. 5 is a flowchart illustrating the exemplary steps of the relational inventory test carried out by the computer system described herein, according to an embodiment of the invention.

The computer is programmed to deliver a narrative report on items that are more elevated than most items in each of the diagnostic categories 3. The report may only reflect items exceeding a given score. Refer to FIG. 5 for a detailed flow chart describing the computerized inventory test and resulting outputs.

With reference to the illustrative embodiment of FIG. 5, it can be seen that the relational inventory (RI) test commences at 200. At step 202, the testee reads the questions of the relational inventory (RI) test. In step 204, the testee answers the questions by clicking on the appropriate response. Then, in step 206, the computer receives and stores the numerical response to the questions. After which, in step 208, the computer calculates and stores a numerical average for each relational characteristic (2, in FIG. 2). In step 210, the computer calculates and stores a numerical average for each diagnostic category (3, in FIG. 2) using the averages computed in step 208. Then, the computer generates and displays a graphic summary of the inventory test (see FIG. 2) in step 212. Finally, in step 214, the computer compares the numerical average of each diagnostic category to a predetermined number, and the computer generates a preprogrammed diagnostic written response based on the predetermined number.

2. Projective Sequence

Figure 10:
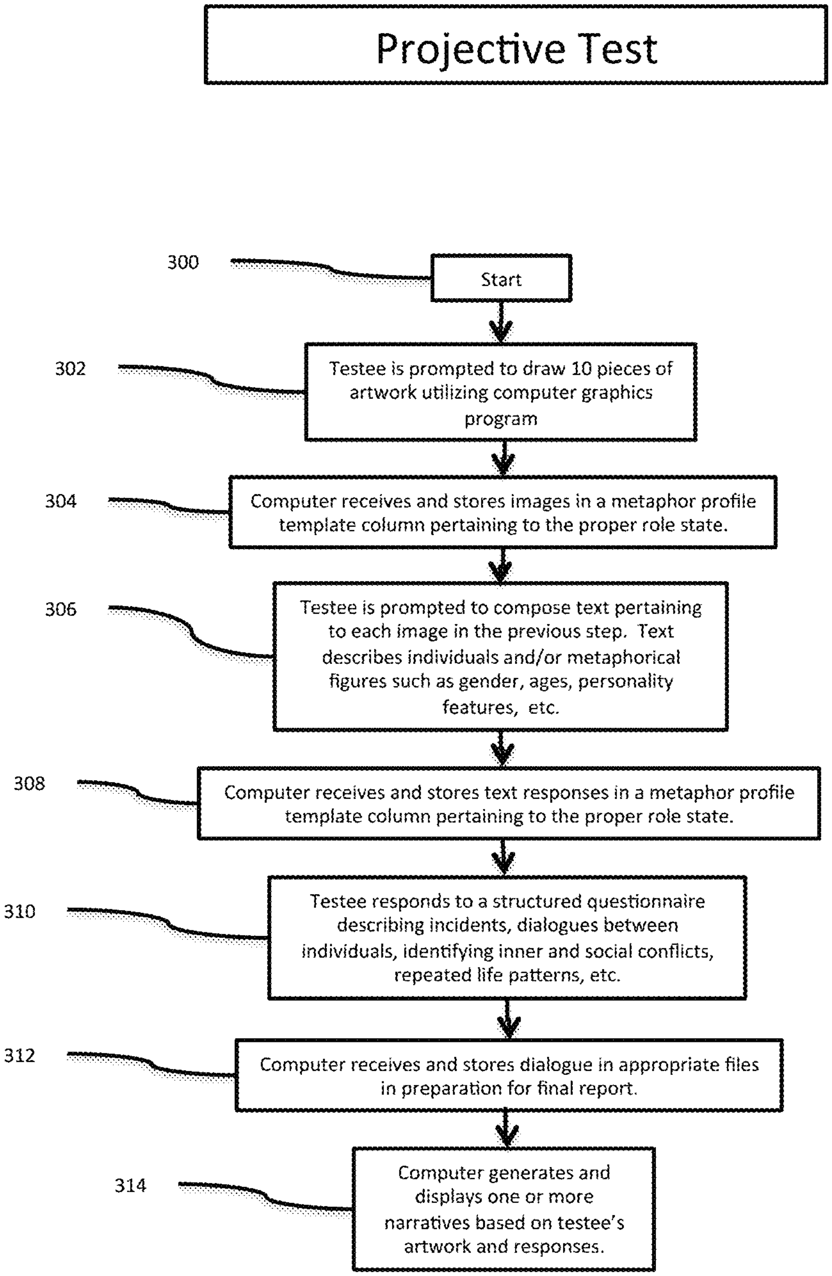
FIG. 10 is a flowchart illustrating the exemplary steps of the projective sequence test carried out by the computer system described herein, according to an embodiment of the invention.

The projective sequence portion of the test is depicted in FIG. 10, and comprises ten artwork assignments, which are all stored in the processor and later illustrated in the final report. With reference to the illustrative embodiment of FIG. 10, it can be seen that the projective sequence test commences at 300. At step 302, the testee is prompted to draw ten (10) pieces of artwork utilizing a computer graphics program or by uploading drawings generated manually using a scanner device operatively coupled to the computer. In step 304, the computer receives and stores the images in a metaphor profile template column pertaining to the proper role state. Then, in step 306, the testee is prompted to compose text pertaining to each image drawn in step 302. In general, the text composed by the testee describes individuals and/or metaphorical figures, such as gender, ages, personality features, etc. After which, in step 308, the computer receives and stores text responses in a metaphor profile template column pertaining to the proper role state. In step 310, the testee responds to a structured questionnaire describing incidents, dialogues between individuals, identifying inner and social conflicts, repeated life patterns, etc. Then, in step 312, the computer receives and stores the dialogue in appropriate files in preparation for the final report. Finally, in step 314, the computer generates and displays one or more narratives based on the testee's artwork and responses.

The topics of the artwork of the projective test include autobiographic experiences and metaphorical creation themes; each exercise is followed by a structured questionnaire with a series of steps seeking to identify the person's relational pattern throughout the tests. For example, one of the projective tests is the Animal Metaphor Test where the testee is asked to draw two (2) animals side-by-side 19 on the computer screen (FIG. 6). The testee is then asked to identify the traits of the animals and prompted to write about a likely conversation between them 20. The computer files the images and the written response to the proper file location related to one of the six role states 16 in FIG. 8.

Figure 7:
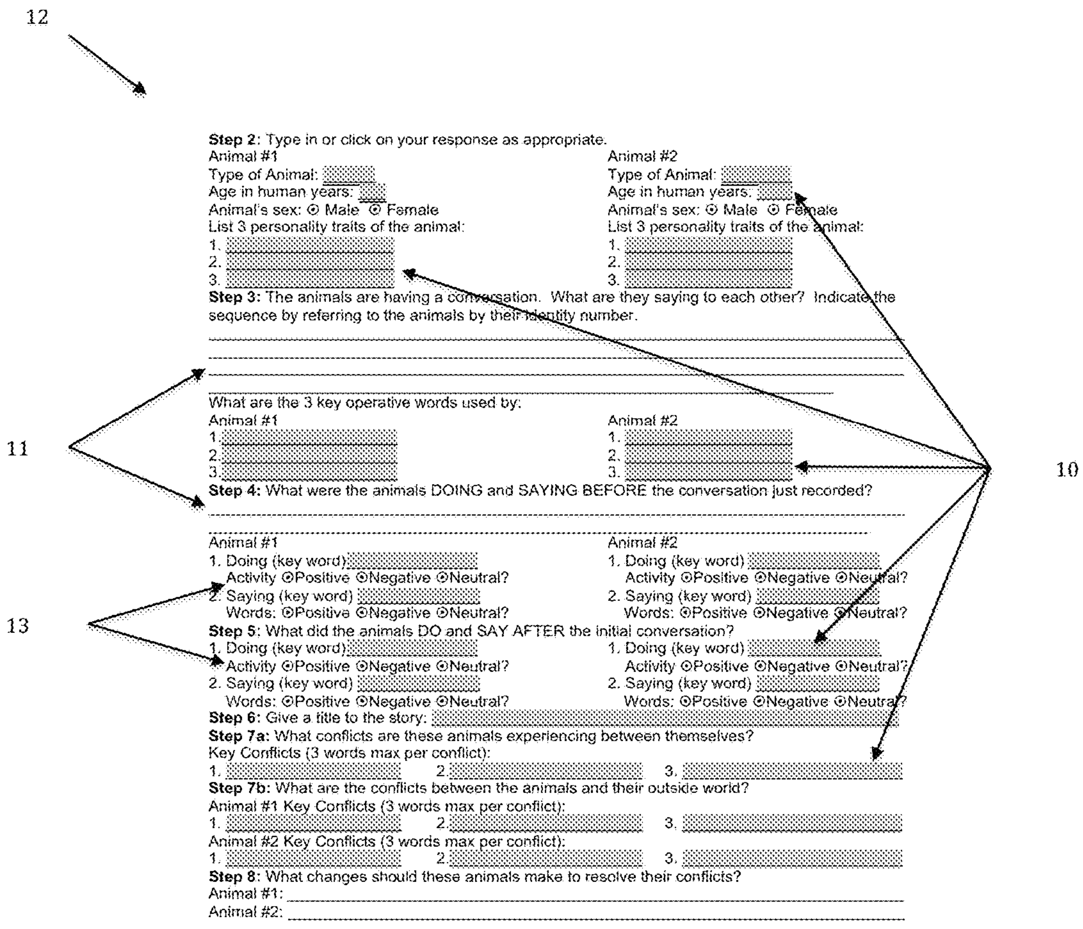
FIG. 7 illustrates an exemplary questionnaire for the animal metaphor subtest, where the testee is instructed to answer questions pertaining to the animal metaphor subtest, according to an embodiment of the invention.
Figure 9:
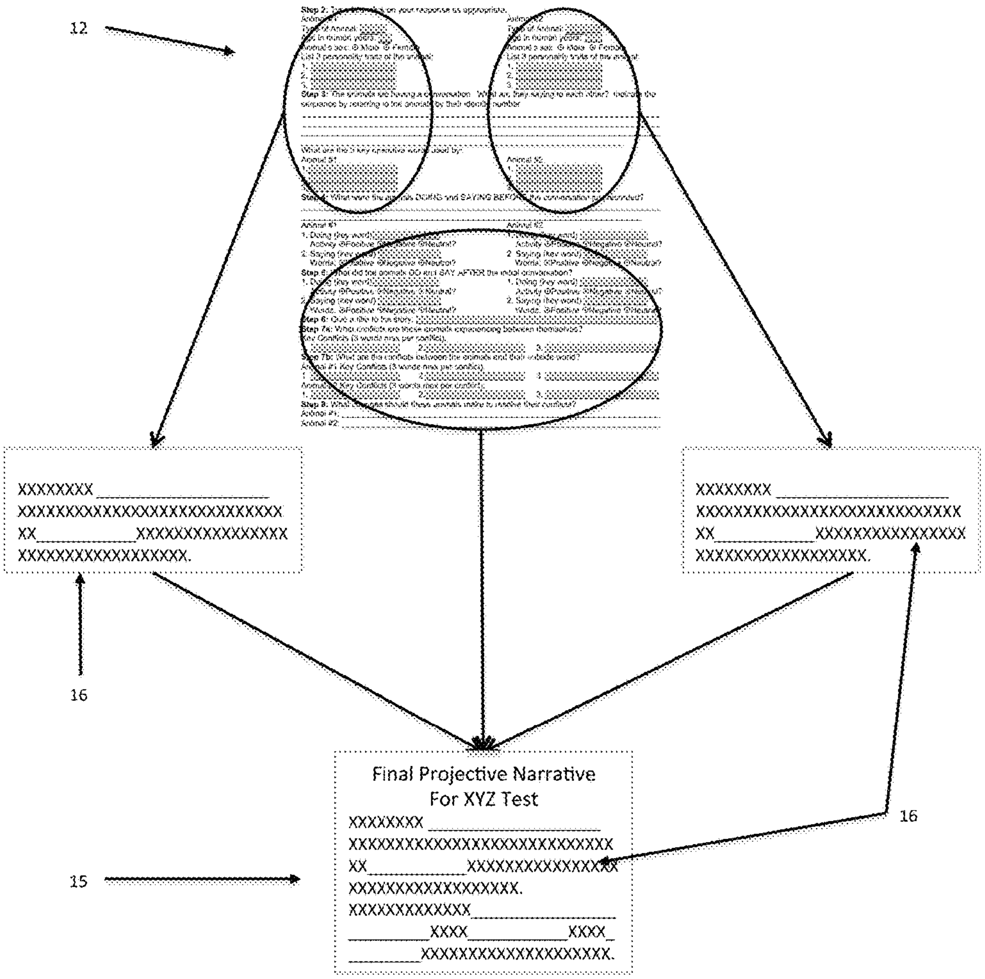
FIG. 9 illustrates the manner in which an exemplary narrative is generated from the responses of the testee to one of the questionnaires of the projective sequence test, according to an embodiment of the invention.

After completing the metaphor drawings for each of the ten projective tests, the testee is prompted to develop a dialogue based on strategic questions that analyze the projective content of each of the drawings. As an example, it is shown in FIG. 7 where the responses are typed. The responses are typed into the shaded areas 10 using the keyboard of the computer. The questions progressively elicit insights into one's relational pattern. The testee is guided to recognize a pattern and also to suggest changes in optimizing resolutions. The computer stores the responses and assigns them to the appropriate role of the six-role template where they are presented to the testee in the final report. Similar to the inventory test narrative 14, the output of each projective test is also a narrative 15 solely captured by the statements of the client and shown in FIG. 9. The narrative is produced by the computer matching the key items, as quotations of the testee, stored in the computer to a predetermined format for their integration with other statements as interpretations provided by the testee.

Figure 8:
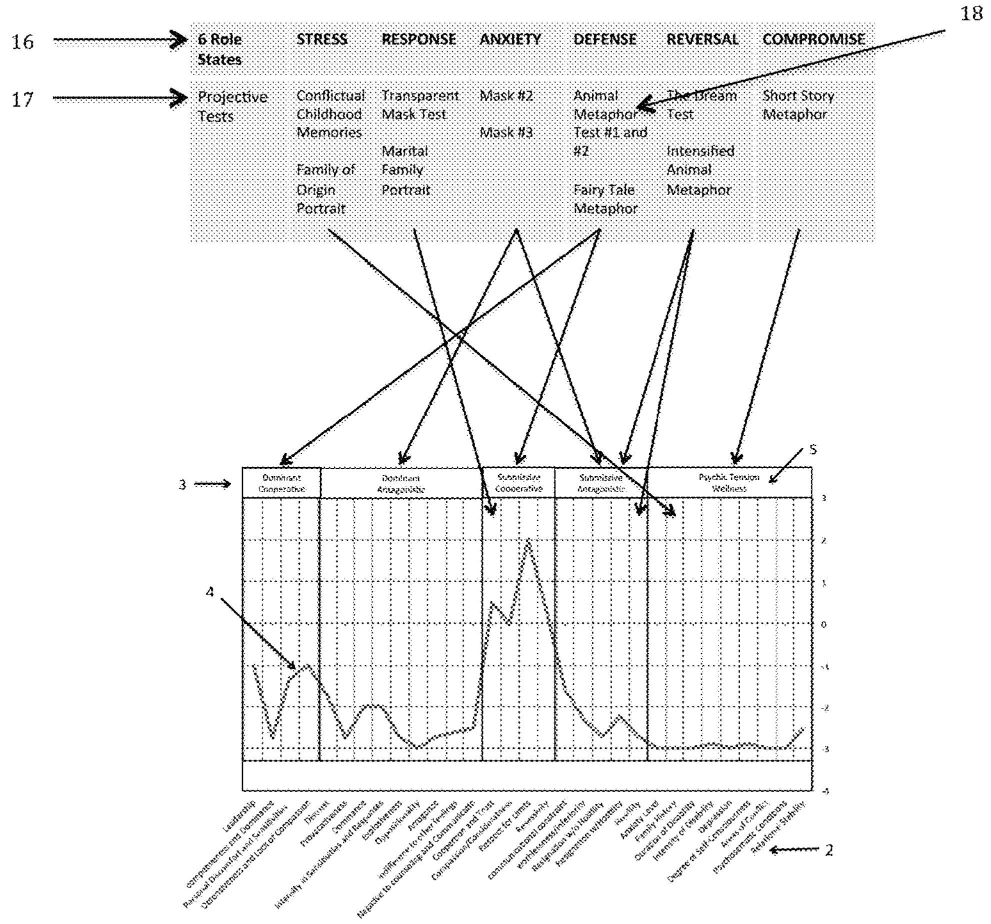
FIG. 8 illustrates some of the relationships between the subtests of the projective sequence test and the diagnostic and psychic tension wellness categories of the relational inventory test, according to an embodiment of the invention.
Figure 12:
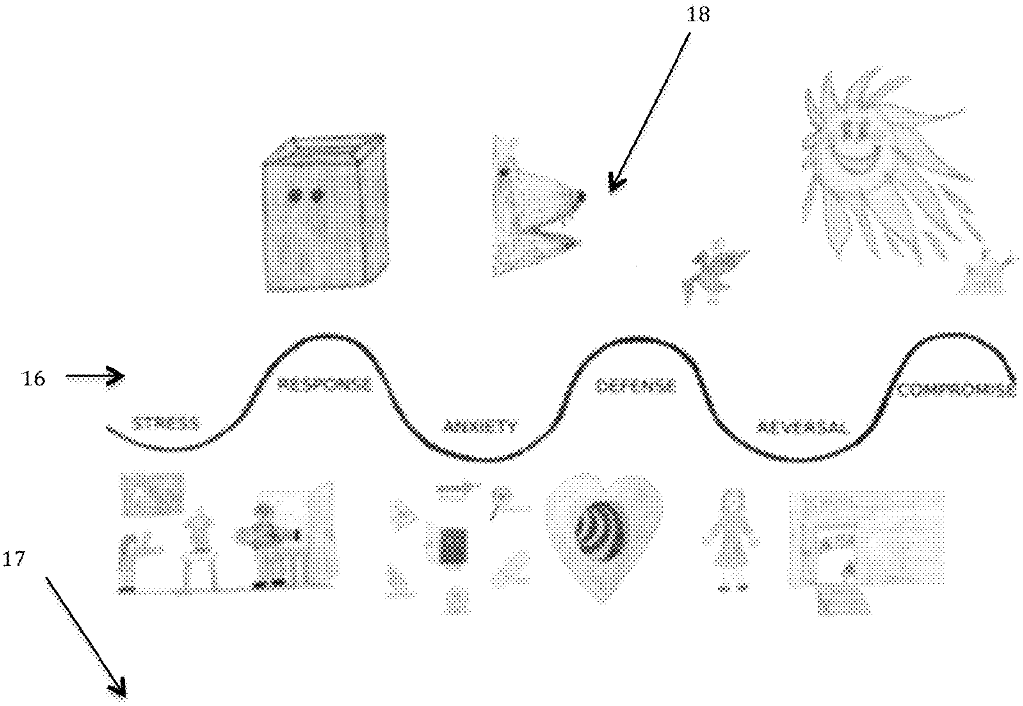
FIG. 12 depicts a sine curve harmonic diagram integrating the test information along the six role states in a syndromal sequence with associated exemplary art and responses provided by a testee, according to an embodiment of the invention.

Each of the projective test results 17 corresponds to one of six role states 16 in a syndromal sequence as shown in FIG. 8 and FIG. 12. The six role states 16 are Stress, Response, Anxiety, Defense, Reversal and Compromise. The projective test results 17 correlate to the relational diagnosis identified in the relational inventory (RI) 1 completed earlier. For example, the Animal Metaphor test 18 highlights the defensive role of the syndromal sequence. It illustrates how a person resolves internal conflicts. Furthermore, the key words and answers provided by the testee and stored by the computer in the Animal Metaphor test provides insights into the overall relational modality of the testee and should have some degree of correlation with the scores of selective communicational and relational traits 2 and diagnostic categories 3 previously stored by the computer in the relational inventory (RI) 1. FIG. 8 shows a diagram of some of these relationships. FIG. 12 shows a diagram of the six role states 16 in a syndromal sequence with associated art and narrative provided by a testee.

The set of projective test results 17 affirm and complement the diagnostic results of the relational inventory (RI) 1. The integration of the projective test results 17 and the narrative results of the relational inventory (RI) 1 transform the fragmented personal experiences into a pattern of conflict resolution that the testee can recognize so he or she can intervene on their own behalf. Assuming personal responsibility through immediate self-awareness makes the process more impactful and meaningful. For example, as shown in FIG. 12, the testee draws images, not necessarily in any particular order, by using a digital pen or mouse, that are seemingly unrelated to any stress or anxiety felt by the testee. At the time the images are drawn and stored by the computer and the associated narratives are written and stored by the computer, it is not fully understood by the testee that there is a cause-effect relationship between the meaning behind the images and any anxiety or stress currently felt by the testee. In the example shown in FIG. 12, as the images are organized and presented in a psychodynamic sequence as dictated by the template in FIG. 17, it turns out that the passing of a loving grandmother was a traumatic event for the testee, thus, a reason for the testee to withdrawal and not pursue higher ambitions in his or her life. Not pursuing a life-goal created anxiety, self-blame and remorse leading him or her to depression and self-destructive conduct. With the self-realization that the grandmother's loss was affecting his or her ability to achieve his or her own dreams, the testee can now go through the process of reversal or healing, which is to understand that the traumatic event should not adversely affect his or her future aspirations, thus removing or at least reducing the devastating feelings of guilt, remorse and self-blame.

With considerable effort and delay, a trained and experienced clinician would be able to review the data supplied in FIG. 1 (the relational inventory) indicating the personality type of submissiveness, hence his or her difficulty expressing feelings and assertiveness together with the projective images and selective narrative as depicted in FIG. 12 in order to reach a diagnosis that could be communicated to the testee. The combined information on his or her relational diagnosis and its manifestation in all the projective tests as the loss of self-confidence is able to lead this patient to insights and changes. Unlike lengthy prior therapies reflecting ineffectiveness of clinical symptom diagnostic categories and therapeutic failures, the computer-based assessment is able to serve as an emotionally effective intervention benefitting the patient and is able to expedite his or her healing. The assessment is able to correct non-relational diagnostic impressions offered by multiple prior clinicians. However, through the relational diagnosis corroborated by the projective testing, the patient is able to benefit and recover from years of suffering and ineffective therapies in a short period of time. The storage of randomly generated narrative and metaphorical images by the computer and the strategic placement of the stored data, a report summary is presented to the testee in real-time. Both the content and sequencing of the report summary provides for heightened self-realization and therefore, self-diagnosis immediately after taking the test. It is understood that immediate self-realization is a more powerful agent for change than a delayed, third party diagnosis.

An example of portions of a computerized report-out to a testee is shown in FIGS. 13-19. Automatically, the report presents the numerical ratings and the metaphorical images allowing the reader to recognize the testee's own relational diagnosis, both quantitatively and qualitatively. The relational inventory (RI) and projective tests cross-validate each other. In one or more embodiments, the computer integrates the test information into a one or two page report first, identifying one's relational modality as a wellness diagnosis and second, by organizing all projective information reflecting how this modality unfolds as a syndromal emotional process logically integrating one's fragmented lifetime experiences into a pattern that one repeats, but which the testee learns to modify to reduce conflicts by optimizing power management. In addition, the single-view report that shows the testee's metaphorical images along with the testee's relational narrative provides a meaningful and non-fragmented summation. Finally, a review by the testee of the relevance of the assessment experience is useful feedback for the tester.

In FIGS. 15-16E, exemplary tabular output generated by the computer-based system for the relational inventory test is illustrated. Specifically, the table presented in the FIG. 15 chart depicts an overall relational modality evaluation scale (RMES) score profile for an exemplary testee. In this figure, the box with the highest score (e.g., the "Submissive Cooperative" box in FIG. 15) indicates the relational modality for the testee. The relational modalities correspond to alternative models of resolving conflict, all of which have strengths and weaknesses. The tables presented in FIGS. 16A-16E present sub-scores for each of the four relational modalities and psychic tension. The sub-scores correspond with more nuanced qualities that characterize the relational modality. Each of these sub-scores is characterized by a descriptive label as well as by a position with the Stress, Response, Anxiety, Defense, Reversal, Compromise dialectic. This pattern is a useful template to chart psychological responses to conflict, thus allowing the testee to identify specific areas to work on making changes.

The exemplary narrative report in FIGS. 13, 14, and 18 includes the insights generated by each metaphor and contrasts them to the corresponding narrative elements. The images and narrative, which were originally created randomly, are integrated and correlated psychodynamically to create a self-revealing life cycle of the testee's experiences. By receiving and reflecting on this information in real-time, the testee is immediately lead to the realization that they own the solution to their anxiety or psychosis without the coaching or counseling of a clinical expert to tell them it requires a change in attitude. Furthermore, any success derived from making the necessary changes is more satisfying to the individual.

FIG. 17 illustrates the template used by the computer to assign metaphorical images and narrative to create a relational diagnosis. That is, the metaphor profile template of FIG. 17 organizes the information provided by the projective tests identifying one's modality illustrated by the artwork. The profile integrates the images of the tests, reconstructing the chain of six interrelated emotions, illustrating the relational pattern producing a visual record of the personality type reconstructing the six-role syndromal process with the images generated in the succession of tasks. The images help to identify continuity in emotions as a person's particular emotional conflict resolution pattern. The person's syndromal sequence of emotions in his or her lifecycle may be bound by one key action with its transformations organized by the six-role process as illustrated in the template. The psychodynamic organization of the images on the template portrays the dramatic connection between the six roles: stress elicits a response, the response elicits anxiety as anticipations of role reversal; anxiety elicits defenses and these the actual role reversal captured in dreams and intensified metaphors; resolutions are presented in short stories.

Further, the computer generates a table of suggested changes in order to remind the test taker of her or his own insights about making changes. An exemplary table of suggested changes is illustrated in FIG. 19. The items reviewed in parallel are: (i) initially accepting responsibility for the pattern, and then (ii) addressing the problematic aspect of the pattern by making appropriate power management changes and finally reflecting on one's willingness to make changes.

A measure of the degree of self-diagnosis and relevancy of the invention is obtained by a survey as shown in FIG. 20.

The computerized survey is done immediately after reading and reviewing the results. The survey assists the tester in validating the content and sequence of the test sections. It also assists the testee in confirming the therapeutic value of the test based on the number of positive and negative responses. Finally, FIG. 21 illustrates the narrative by the testee that reaffirms his or her commitment to making the necessary attitudinal changes.

Although the invention has been shown and described with respect to a certain embodiment or embodiments, it is apparent that this invention can be embodied in many different forms and that many other modifications and variations are possible without departing from the spirit and scope of this invention.

Moreover, while exemplary embodiments have been described herein, one of ordinary skill in the art will readily appreciate that the exemplary embodiments set forth above are merely illustrative in nature and should not be construed as to limit the claims in any manner. Rather, the scope of the invention is defined only by the appended claims and their equivalents, and not, by the preceding description.

In one or more embodiments, the invention has three functions: (1) it is didactic with an introductory essay introducing the two key concepts of the Formal Theory: the notion of the conflict resolution unconscious, its scientific structure and moral conflict resolving self-adjustive function; (2) it is diagnostic leading the test taker to identify one's relational modality and its syndromal unfolding; (3) finally it is therapeutic by allowing the person to reduce psychic conflicts, by increasing one's self-awareness and by identifying changes that modify one's effectiveness in dealing with conflicts.

The didactic function consists of an introductory essay offered to the test taker prior to beginning the self-assessment process and of an essay with information regarding the testing experience and its findings following the completion of the assessment. The essays are offered to the test taker along with the report summing up the assessment findings.

The invention claimed is:

1. A computer-based system for relational modality assessment with projective testing, said system including:

a computer system comprising a computer operably associated with a local input device located proximate to the computer, a visual display device, and memory storing executable instructions, the computer being specially programmed to perform the operations of:

generating a relational inventory test comprising a plurality of questions pertaining to a plurality of diagnostic categories, and displaying said plurality of questions of said relational inventory test on said visual display device so that said plurality of questions are viewable by a system user;

receiving, at the local input device, answers to said plurality of questions of said relational inventory test from said system user;

generating a quantitative assessment of one or more of said plurality of diagnostic categories based upon said answers of said system user to said plurality of questions of said relational inventory test;

outputting said quantitative assessment of said one or more of said plurality of diagnostic categories for said system user on said visual display device;

generating a projective sequence test comprising a plurality of artwork assignments and corresponding questionnaires pertaining to a plurality of role states, and displaying said artwork assignments and said corresponding questionnaires of said projective sequence test on said visual display device so that said artwork assignments and said corresponding questionnaires are viewable by a system user;

receiving, at the local input device, a plurality of drawings elicited by said artwork assignments and a plurality of responses to said corresponding questionnaires from said system user, said plurality of drawings received at said local input device being drawn by said system user, and said plurality of drawings and said plurality of responses being stored by said computer in profile template entries corresponding to respective ones of said plurality of role states;

generating a structured output report pertaining to two or more of said plurality of role states based upon said plurality of drawings and said plurality of responses of said system user to said plurality of artwork assignments and said corresponding questionnaires of said projective sequence test, said structured output report being generated by said computer based upon said profile template entries such that said plurality of drawings and said plurality of responses are arranged psychodynamically so as to create a self-revealing life cycle of said system user's experiences in real-time; and outputting said structured output report pertaining to said plurality of role states for said system user on said visual display device;

wherein the integration of the results of said relational inventory test and the results of said projective sequence test transform fragmented personal experiences of said system user into a pattern of conflict resolution that said system user is able to recognize so that he or she is able to intervene on his or her own behalf; and wherein, based upon said quantitative assessment generated from said results of said relational inventory test and said structured output report generated from said results of said projective sequence test, said system user is capable of self-diagnosing his or her psychological state.

2. The computer-based system according to claim 1, wherein said plurality of questions of said relational inventory test includes subsets of questions directed to particular relational characteristics, wherein said answers to said plurality of questions of said relational inventory test comprise numerical level of agreement values, and wherein, prior to the operation of generating said quantitative assessment of said one or more of said plurality of diagnostic categories, said computer is further specially programmed to perform the operation of:

computing one or more numerical averages of said numerical level of agreement values corresponding to respective one or more said particular relational characteristics.

3. The computer-based system according to claim 2, wherein, after the operation of computing one or more numerical averages of said numerical level of agreement values corresponding to said respective one or more said particular relational characteristics, said computer is further specially programmed to perform the operation of:

computing one or more additional numerical averages for one or more of said plurality of diagnostic categories using said one or more numerical averages computed for said one or more particular relational characteristics.

4. The computer-based system according to claim 3, wherein said quantitative assessment of said one or more of said plurality of diagnostic categories is based upon said one or more additional numerical averages computed for said one or more of said plurality of diagnostic categories, and wherein the operation of generating said quantitative assessment of said one or more of said plurality of diagnostic categories comprises generating a graphical results summary of said relational inventory test that describes characteristics of said psychological state of said system user.

5. The computer-based system according to claim 4, wherein, after the operation of generating said graphical results summary of said relational inventory test, said computer is further specially programmed to perform the operation of:

generating, based upon said one or more computed additional numerical averages for said one or more of said plurality of diagnostic categories, one or more diagnostic narratives corresponding to respective ones of said one or more computed additional numerical averages; and outputting said one or more diagnostic narratives on said visual display device so that said one or more diagnostic narratives are viewable by said system user.

6. The computer-based system according to claim 1, wherein said plurality of diagnostic categories of said plurality of questions of said relational inventory test comprise a plurality of categories corresponding to respective relational modalities and a category pertaining to psychic tension and/or wellness.

7. The computer-based system according to claim 1, wherein said plurality of role states of said projective sequence test comprises at least one of: (i) stress, (ii) response, (iii) anxiety, (iv) defense, (v) reversal, and (vi) compromise.

8. The computer-based system according to claim 7, wherein said projective sequence test comprises a plurality of individual projective subtests, each of said plurality of individual projective subtests pertaining to one of said plurality of role states.

9. The computer-based system according to claim 8, wherein said plurality of individual projective subtests comprises at least one of: (i) a subtest pertaining to a childhood conflict, (ii) a subtest pertaining to an adolescent conflict, (iii) a subtest pertaining to a transparent mask of testee, (iv) a subtest pertaining to a feelings mask of the testee, (v) a subtest pertaining to what is in the heart of the testee, (vi) a subtest pertaining to a first type of animal metaphor, (vii) a subtest pertaining to a second type of animal metaphor, (viii) a subtest pertaining to a fairy tale metaphor, (ix) a subtest pertaining to a dream metaphor, and (x) a subtest pertaining to a short story metaphor; and wherein each of said plurality of artwork assignments and said corresponding questionnaires pertain to a respective one of said individual projective subtests.

10. The computer-based system according to claim 1, wherein, after the operation of receiving said plurality of drawings elicited by said artwork assignments and said plurality of responses to said corresponding questionnaires from said system user, said computer is further specially programmed to perform the operation of:

generating, based upon said plurality of responses to said corresponding questionnaires, one or more projective narratives that at least partially describe said psychological state of said system user; and outputting said one or more projective narratives on said visual display device so that said one or more projective narratives are viewable by said system user.

11. The computer-based system according to claim 1, wherein said local input device comprises a keyboard and at least one of: (i) a mouse, (ii) a digital pen or stylus, and (iii) a scanner device; and wherein the operation of receiving said plurality of drawings elicited by said artwork assignments comprises receiving said plurality of drawings generated using said mouse, generated using said digital pen or stylus, or uploaded using said scanner device.

12. A computer-based system for relational modality assessment with projective testing, said system including:

a computer system comprising a computer operably associated with a local input device located proximate to the computer, a visual display device, and memory storing executable instructions, the computer being specially programmed to perform the operations of:

generating a relational inventory test comprising a plurality of questions pertaining to a plurality of diagnostic categories, said plurality of diagnostic categories of said plurality of questions including a plurality of categories corresponding to respective relational modalities and a category pertaining to psychic tension and/or wellness, and displaying said plurality of questions of said relational inventory test on said visual display device so that said plurality of questions are viewable by a system user;

receiving, at the local input device, answers to said plurality of questions of said relational inventory test from said system user;

generating a quantitative assessment of one or more of said plurality of diagnostic categories based upon said answers of said system user to said plurality of questions of said relational inventory test;

outputting said quantitative assessment of said one or more of said plurality of diagnostic categories for said system user on said visual display device;

generating a projective sequence test comprising a plurality of artwork assignments and corresponding questionnaires pertaining to a plurality of role states, said plurality of role states including at least two of: (i) stress, (ii) response, (iii) anxiety, (iv) defense, (v) reversal, and (vi) compromise, and displaying said artwork assignments and said corresponding questionnaires of said projective sequence test on said visual display device so that said artwork assignments and said corresponding questionnaires are viewable by a system user;

receiving, at the local input device, a plurality of drawings elicited by said artwork assignments and a plurality of responses to said corresponding questionnaires from said system user, said plurality of drawings received at said local input device being drawn by said system user, and said plurality of drawings and said plurality of responses being stored by said computer in profile template entries corresponding to respective ones of said plurality of role states;

generating a structured output report pertaining to two or more of said plurality of role states based upon said plurality of drawings and said plurality of responses of said system user to said plurality of artwork assignments and said corresponding questionnaires of said projective sequence test, said structured output report being generated by said computer based upon said profile template entries such that said plurality of drawings and said plurality of responses are arranged psychodynamically so as to create a self-revealing life cycle of said system user's experiences in real-time; and outputting said structured output report pertaining to said plurality of role states for said system user on said visual display device;

wherein the integration of the results of said relational inventory test and the results of said projective sequence test transform fragmented personal experiences of said system user into a pattern of conflict resolution that said system user is able to recognize so that he or she is able to intervene on his or her own behalf; and wherein, based upon said quantitative assessment generated from said results of said relational inventory test and said structured output report generated from said results of said projective sequence test, said system user is capable of self-diagnosing his or her psychological state.

13. The computer-based system according to claim 12, wherein said plurality of questions of said relational inventory test includes subsets of questions directed to particular relational characteristics, wherein said answers to said plurality of questions of said relational inventory test comprise numerical level of agreement values, and wherein, prior to the operation of generating said quantitative assessment of said one or more of said plurality of diagnostic categories, said computer is further specially programmed to perform the operation of:

computing one or more numerical averages of said numerical level of agreement values corresponding to respective one or more said particular relational characteristics.

14. The computer-based system according to claim 13, wherein, after the operation of computing one or more numerical averages of said numerical level of agreement values corresponding to said respective one or more said particular relational characteristics, said computer is further specially programmed to perform the operation of:

computing one or more additional numerical averages for one or more of said plurality of diagnostic categories using said one or more numerical averages computed for said one or more particular relational characteristics.

15. The computer-based system according to claim 14, wherein said quantitative assessment of said one or more of said plurality of diagnostic categories is based upon said one or more additional numerical averages computed for said one or more of said plurality of diagnostic categories, and wherein the operation of generating said quantitative assessment of said one or more of said plurality of diagnostic categories comprises generating a graphical results summary of said relational inventory test that describes characteristics of said psychological state of said system user.

16. The computer-based system according to claim 15, wherein, after the operation of generating said graphical results summary of said relational inventory test, said computer is further specially programmed to perform the operation of:

generating, based upon said one or more computed additional numerical averages for said one or more of said plurality of diagnostic categories, one or more diagnostic narratives corresponding to respective ones of said one or more computed additional numerical averages; and outputting said one or more diagnostic narratives on said visual display device so that said one or more diagnostic narratives are viewable by said system user.

17. The computer-based system according to claim 12, wherein said projective sequence test comprises a plurality of individual projective subtests, each of said plurality of individual projective subtests pertaining to one of said plurality of role states.

18. The computer-based system according to claim 17, wherein said plurality of individual projective subtests comprises at least one of: (i) a subtest pertaining to a childhood conflict, (ii) a subtest pertaining to an adolescent conflict, (iii) a subtest pertaining to a transparent mask of testee, (iv) a subtest pertaining to a feelings mask of the testee, (v) a subtest pertaining to what is in the heart of the testee, (vi) a subtest pertaining to a first type of animal metaphor, (vii) a subtest pertaining to a second type of animal metaphor, (viii) a subtest pertaining to a fairy tale metaphor, (ix) a subtest pertaining to a dream metaphor, and (x) a subtest pertaining to a short story metaphor; and wherein each of said plurality of artwork assignments and said corresponding questionnaires pertain to a respective one of said individual projective subtests.

19. The computer-based system according to claim 12, wherein, after the operation of receiving said plurality of drawings elicited by said artwork assignments and said plurality of responses to said corresponding questionnaires from said system user, said computer is further specially programmed to perform the operation of:

generating, based upon said plurality of responses to said corresponding questionnaires, one or more projective narratives that at least partially describe said psychological state of said system user; and outputting said one or more projective narratives on said visual display device so that said one or more projective narratives are viewable by said system user.

20. The computer-based system according to claim 12, wherein said local input device comprises a keyboard and at least one of: (i) a mouse, (ii) a digital pen or stylus, and (iii) a scanner device; and wherein the operation of receiving said plurality of drawings elicited by said artwork assignments comprises receiving said plurality of drawings generated using said mouse, generated using said digital pen or stylus, or uploaded using said scanner device.

* * * * *